(12) United States Patent
Burke et al.

(10) Patent No.: US 10,072,028 B2
(45) Date of Patent: Sep. 11, 2018

(54) CROSS-COUPLING OF UNACTIVATED SECONDARY BORONIC ACIDS

(71) Applicant: The Board of Trustees of the University of Illinois, Urbana, IL (US)

(72) Inventors: Martin D. Burke, Champaign, IL (US); Pulin Wang, Austin, TX (US); Ian Crouch, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 15/034,102

(22) PCT Filed: Nov. 3, 2014

(86) PCT No.: PCT/US2014/063692
§ 371 (c)(1),
(2) Date: May 3, 2016

(87) PCT Pub. No.: WO2015/066612
PCT Pub. Date: May 7, 2015

(65) Prior Publication Data
US 2016/0280721 A1 Sep. 29, 2016

Related U.S. Application Data

(60) Provisional application No. 61/899,296, filed on Nov. 3, 2013.

(51) Int. Cl.
*C07F 5/02* (2006.01)
*C07C 67/343* (2006.01)
(Continued)

(52) U.S. Cl.
CPC .............. *C07F 5/025* (2013.01); *C07B 37/04* (2013.01); *C07C 1/321* (2013.01); *C07C 67/343* (2013.01); *C07B 2200/07* (2013.01); *C07C 2523/50* (2013.01); *C07C 2531/24* (2013.01); *C07C 2601/02* (2017.05); *C07C 2601/04* (2017.05); *C07C 2601/08* (2017.05);
(Continued)

(58) Field of Classification Search
None
See application file for complete search history.

(56) References Cited

FOREIGN PATENT DOCUMENTS

| WO | WO-2009014550 A1 | 1/2009 |
| WO | WO-2013149997 A1 | 10/2013 |

OTHER PUBLICATIONS

Brown ("Chiral synthesis via organoboranes: XVI. Boroxazolidones derived from alpha-amino acids and borinic or boronic esters. A simple procedure for upgrading borinates and boronates to materials of high optical purity" Journal of Organometallic Chemistry, vol. 341, 1988, p. 73-81) (Year: 1988).*

(Continued)

*Primary Examiner* — Jafar Parsa
*Assistant Examiner* — Amy C Bonaparte
(74) *Attorney, Agent, or Firm* — Foley Hoag LLP; Dana M. Gordon

(57) ABSTRACT

Provided are methods for site- and stereo-retentive cross-couplings with unactivated secondary boronic acids, which methods are particularly useful in building block-based approach for small molecule synthesis. Also provided is a method of forming an air-stable chiral secondary boronic acid.

26 Claims, 2 Drawing Sheets

Scheme 2

(51) Int. Cl.
  *C07B 37/04* (2006.01)
  *C07C 1/32* (2006.01)
(52) U.S. Cl.
  CPC ...... *C07C 2601/14* (2017.05); *C07C 2601/16* (2017.05); *C07C 2602/10* (2017.05)

(56) References Cited

OTHER PUBLICATIONS

Li ("Pinene-Derived Iminodiacetic Acid (PIDA): A Powerful Ligand for Stereoselective Synthesis and Iterative Cross-Coupling of C(sp3) Boronate Building Blocks" J. Am. Chem. Soc., 133, 2011, p. 13774-13777) (Year: 2011).*

Kuritani ("Organic and Organometallic Nanofibers Formed by Supramolecular Assembly of Diamond-Shaped Macrocyclic Ligands and Pdll complexes" Chemistry, An Asian Journal, vol. 8, issue 7, first published Jun. 20, 2013, p. 1368-1371 and p. S1-S24 of supporting information) (Year: 2013).*

McQuarrie ("Appendix E: Data for Selected Acids and Bases" General Chemistry, Fourth Edition, 2011, p. A29-A31) (Year: 2011).*

Sene ("Boronate Ligands in Materials: Determining Their Local Environment by Using a Combination of IR/Solid-State NMR Spectroscopies and DFT Calculations" Chemistry, a European Journal, 19(3), p. 880-891, 2013).*

Dreher et al., "Efficient Cross-Coupling of Secondary Alkyltrifluoroborates with Aryl Chlorides: Reaction Discovery Using Parallel Microscale Experimentation," J. Am. Chem. Soc., 130(29) 9257-9259 (2008).

Garlapati et al., "Development of [alpha]-glucosidase inhibitors by room temperature C-C cross couplings of quinazolinones," Organic Biomolecular Chem, 11(29): 4778 (2013).

Li et al., "Pinene-Derived Iminodiacetic Acid (PIDA): Powerful Ligand for Stereoselective Synthesis and Iteractive Cross-Coupling of C(sp 3) Boronate Building Blocks," J. Am. Chem Soc., 133(35): 13774-13777 (2011).

Li et al., "Stereospecific Pd-Catalyzed Cross Coupling Reactions of Secondary Alkylboron Nucleophiles and Aryl Chlorides," J. Am. Chem. Soc., 136(40) 14027-14030 (2014).

Sene et al., "Boronate Ligands in Materials: Determining Their Local Enviroment by Using a Combination of IR/Solid-State NMR Spectroscopies and DFT Calculations," Chemistry—EU J, 19(3) 880-891 (2013).

Zou G et al., "Ag(I)-promoted Suzuki-Miyaura cross-couplings of n-alkylboronic acids," Tetrahedron Letters, 42(41) 7213-7215 (2001).

* cited by examiner

Scheme 1

Scheme 2

Scheme 3

CROSS-COUPLING OF UNACTIVATED SECONDARY BORONIC ACIDS

RELATED APPLICATIONS

This application is the U.S. National Stage of PCT/US2014/063692, filed Nov. 3, 2014, which claims benefit of U.S. Provisional Patent Application No. 61/899,296, filed Nov. 3, 2013.

STATEMENT REGARDING FEDERALLY SPONSORED RESEARCH OR DEVELOPMENT

This invention was made with government support under contract number GM080436 awarded by the National Institutes of Health. The government has certain rights in the invention.

BACKGROUND OF THE INVENTION

The Suzuki-Miyaura reaction is a palladium- or nickel-catalyzed cross coupling between a boronic acid or a boronic ester and an organohalide or an organo-pseudohalide. Miyaura, A. *Chem. Rev.,* 1995. This cross coupling transformation is a powerful method for C—C bond formation in complex molecule synthesis. The reaction is tolerant of functional groups and has become increasingly general and widespread in its use for coupling of organic compounds. Barder, T. E. et al., *J. Am. Chem. Soc.* 2005, 127, 4685-4696; Billingsley, K. et al., *J. Am. Chem. Soc.* 2007, 129, 3358-3366; Littke, A. F. et al., *J. Am. Chem. Soc.* 2000, 122, 4020-4028; Nicolaou, K. C. et al., *Angew. Chem. Int. Ed.* 2005, 44, 4442-4489.

Boronic acids are notoriously sensitive to many common reagents. Hall, D. G., *Boronic Acids,* Wiley-VCH, Germany, 2005, pp. 3-14; Tyrell, E. et al., *Synthesis* 2003, 4, 469-483. It is therefore typical to introduce the boronic acid functional group during the last step of a building block synthesis. However, many of the methods for doing so (hydroboration, trapping organometallic reagents with trimethylborate, etc.) are intolerant to a variety of common functional groups, such as alcohols, aldehydes, ketones, alkynes and olefins. This makes the synthesis of structurally complex boronic acid building blocks quite challenging.

Peptides, oligonucleotides, and increasingly oligosaccharides can be rapidly and flexibly prepared in the laboratory from readily accessible building blocks having all of the required site- and stereochemical information pre-installed.[1] The inherent modularity of many small molecules and the rapidly expanding scope of boronic acid cross-coupling chemistry[2-4] collectively support the notion that an analogous building block-based approach for small molecule synthesis may be attainable.[5] However, at present, unactivated Csp$^3$ organoboronates cannot be cross-coupled with the same levels of efficiency, site-, and stereo-retention that is now accessible with many of their Csp$^2$ and activated Csp$^3$ hybridized counterparts.[2-4] Solving this problem stands to enable a wide range of stereochemically complex natural products and Csp$^3$-rich pharmaceuticals[7] to be more efficiently and flexibly prepared via the simple site- and stereo-retentive assembly of off- U.S. Pat. No. 8,013,203 (incorporated by reference), U.S. Pat. No. 8,318,983 (incorporated by reference), and US 2013/0296573 (incorporated by reference), each to Burke et al., disclose protected organoboronic acid compounds comprising a boron having an sp$^3$ hybridization, a conformationally rigid protecting group bonded to the boron, and an organic group bonded to the boron through a boron-carbon bond; methods of making same; and methods of performing chemical reactions using same. In an embodiment, the protected organoboronic acid is an N-methyliminodiacetic acid (MIDA) boronate.

U.S. Pat. No. 8,338,601 (incorporated by reference) and US 2013/0317223 (incorporated by reference), each to Burke et al., disclose methods of performing chemical reactions using protected organoboronic acid compounds. In an embodiment, the protected organoboronic acid is a MIDA boronate. In an embodiment, the reaction is a cross-coupling reaction.

U.S. Pat. No. 8,557,980 (incorporated by reference) and US 2014/0073785 (incorporated by reference), each to Burke et al., disclose methods of forming protected boronic acids that provide a wide variety of building blocks for use in chemical reactions. In an embodiment, the protected boronic acid is a MIDA boronate. In an embodiment, the reaction is a cross-coupling reaction.

US 2013/0243670 (incorporated by reference) to Burke et al. discloses methods and an apparatus for purification of MIDA boronates and deprotection of boronic acids from their MIDA ligands to perform cross-coupling reactions. Iterative cycles of deprotection, coupling, and purification can be used to synthesize small molecules.

US 2014/0094615 (incorporated by reference) to Burke et al. discloses methods of making and using chiral, non-racemic protected organoboronic acid compounds to direct and enable stereoselective synthesis of organic molecules. In an embodiment, the chiral, non-racemic protected organoboronic acid compounds are chiral derivatives of iminodiacetic acid (IDA).

SUMMARY OF THE INVENTION

One aspect of the invention is a method for site- and stereo-retentive cross-couplings of an aryl halide with an unactivated secondary boronic acid. The method is characterized by mild reaction conditions, operationally simplicity, and the use of an air-stable and commercially available catalyst. The method can employ chiral non-racemic boronic acids, which are readily prepared via resolution with a non-racemic chiral substituted iminodiacetic acid (IDA). Taken together the steps of resolution and cross-coupling represent an important step towards adding stereogenic secondary carbon-containing fragments to the growing list of substructures compatible with a general, building block-based approach to the synthesis of small molecules.

An aspect of the invention is a method of forming a product represented by R$^1$R$^2$CH-Ar, comprising:

combining a secondary boronic acid represented by R$^1$R$^2$CH—B(OH)$_2$; an aryl halide represented by Ar-X; a Pd catalyst; a ligand; and Ag$_2$O:

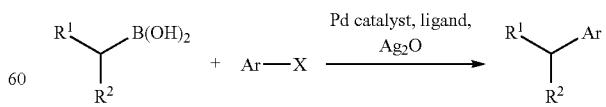

wherein, independently for each occurrence,

R$^1$ and R$^2$ are selected from the group consisting of substituted C$_1$-C$_6$ alkyl and unsubstituted C$_1$-C$_6$ alkyl; or R$^1$ and R$^2$, taken together with the carbon to which they are joined, form a substituted or unsubstituted C$_3$-C$_8$ cycloalkyl;

Ar represents a substituted or unsubstituted monocyclic or polycyclic aryl;

X represents halogen;

Pd catalyst represents Pd(0) or Pd(II);

ligand is P(o-R-phenyl)$_3$; and

R represents $C_1$-$C_4$ alkyl;

thereby forming a product represented by $R^1R^2$CH-Ar.

In certain embodiments, the secondary boronic acid is achiral.

In certain embodiments, the secondary boronic acid is chiral.

In certain embodiments, the secondary boronic acid is a racemic mixture.

In certain embodiments, the secondary boronic acid is not a racemic mixture.

In certain embodiments, the secondary boronic acid has an enantiomeric excess of at least 80 percent. In certain embodiments, the secondary boronic acid has an enantiomeric excess of at least 90 percent. In certain embodiments, the secondary boronic acid has an enantiomeric excess of at least 95 percent.

In certain embodiments, the product represented by $R^1R^2$CH-Ar is not a racemic mixture.

In certain embodiments, the product represented by $R^1R^2$CH-Ar has an enantiomeric excess of at least 80 percent. In certain embodiments, the product represented by $R^1R^2$CH-Ar has an enantiomeric excess of at least 90 percent. In certain embodiments, the product represented by $R^1R^2$CH-Ar has an enantiomeric excess of at least 95 percent.

An aspect of the invention is a method of forming an air-stable chiral secondary boronic acid, wherein the air-stable chiral secondary boronic acid is not a racemic mixture, comprising:

combining a chiral secondary boronic acid represented by formula (I)

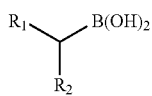
(I)

wherein, independently for each occurrence, $R^1$ and $R^2$ are selected from the group consisting of substituted $C_1$-$C_6$ alkyl and unsubstituted $C_1$-$C_6$ alkyl; a chiral iminodiacetic acid, wherein the chiral iminodiacetic acid is not a racemic mixture; a weak acid catalyst; and a polar aprotic solvent, thereby forming a mixture of chiral boronates;

resolving the mixture of chiral boronates into individual diastereomers; and hydrolyzing an individual diastereomer, thereby forming an air-stable chiral secondary boronic acid, wherein the air-stable chiral secondary boronic acid is not a racemic mixture.

In certain embodiments, the chiral iminodiacetic acid has an enantiomeric excess of at least 80 percent. In certain embodiments, the chiral iminodiacetic acid has an enantiomeric excess of at least 90 percent. In certain embodiments, the chiral iminodiacetic acid has an enantiomeric excess of at least 95 percent.

In certain embodiments, the chiral iminodiacetic acid is benzylcyclopentyl iminodiacetic acid (BIDA).

In certain embodiments, the chiral secondary boronic acid represented by formula (I) is a racemic mixture.

In certain embodiments, the chiral secondary boronic acid represented by formula (I) is not a racemic mixture.

In certain embodiments, the air-stable chiral secondary boronic acid has an enantiomeric excess of at least 80 percent. In certain embodiments, the air-stable chiral secondary boronic acid has an enantiomeric excess of at least 90 percent. In certain embodiments, the air-stable chiral secondary boronic acid has an enantiomeric excess of at least 95 percent.

An aspect of the invention is a method of forming an air-stable trihydroxyborate salt of a primary or secondary boronic acid, comprising:

(i) combining a primary or secondary boronate represented by formula (II):

(II)

a first polar aprotic solvent, and aqueous hydroxide, thereby forming a primary or secondary boronic acid represented by formula (I):

(I)

wherein, independently for each occurrence, $R^1$ is selected from the group consisting of substituted $C_1$-$C_6$ alkyl and unsubstituted $C_1$-$C_6$ alkyl;

$R^2$ is selected from the group consisting of H, substituted $C_1$-$C_6$ alkyl and unsubstituted $C_1$-$C_6$ alkyl; and $R^a$ and $R^b$ are selected from the group consisting of optionally substituted alkyl, aryl, and acyl; or $R^a$ and $R^b$ taken together with the —O—B(CHR$^1$R$^2$)—O— moiety to which they are attached form an optionally substituted heterocyclic ring consisting of 5-10 heavy atoms in the backbone of said heterocyclic ring, wherein 3-5 heteroatoms selected independently from the group consisting of B, O, and N are present in said heterocyclic ring; and (ii) combining the primary or secondary boronic acid represented by formula (I), an ether, and concentrated hydroxide, thereby forming an air-stable trihydroxyborate salt of a primary or secondary boronic acid.

In certain embodiments, the method further comprises combining the air-stable trihydroxyborate salt of a primary or secondary boronic acid, a Lewis acid, and a second polar aprotic solvent, thereby re-forming the primary or secondary boronic acid represented by formula (I).

In certain embodiments, the primary or secondary boronate represented by formula (II) is achiral.

In certain embodiments, the primary or secondary boronic acid represented by formula (I) is a primary boronic acid.

In certain embodiments, the primary or secondary boronic acid represented by formula (I) is a secondary boronic acid.

In certain embodiments, the primary or secondary boronate represented by formula (II) is chiral.

In certain embodiments, the chiral primary or secondary boronate represented by formula (II) is a racemic mixture.

In certain embodiments, the chiral primary or secondary boronate represented by formula (II) is not a racemic mixture.

In certain embodiments, the air-stable salt of the primary or secondary boronic acid is a chiral air-stable salt of the secondary boronic acid.

In certain embodiments, the chiral air-stable salt of the secondary boronic acid is a racemic mixture.

In certain embodiments, the chiral air-stable salt of the secondary boronic acid is not a racemic mixture.

In certain embodiments, the chiral air-stable salt of the secondary boronic acid has an enantiomeric excess of at least 80 percent.

An aspect of the invention is a method of forming a boronic acid, comprising the steps represented by:

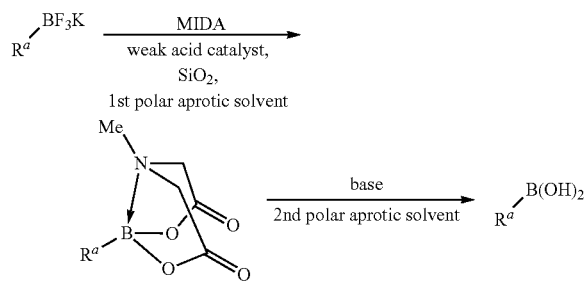

wherein $R^a$ represents an organic group; and

MIDA represents N-methyliminodiacetic acid.

In certain embodiments, the organic group is a chiral organic group; and the boronic acid

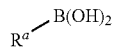

is a chiral boronic acid.

In certain embodiments, the chiral organic group is a racemic mixture; and the chiral boronic acid is a racemic mixture.

In certain embodiments, the chiral organic group is not a racemic mixture; and the chiral boronic acid is not a racemic mixture.

In certain embodiments, the chiral organic group has an enantiomeric excess of at least 80 percent. In certain embodiments, the chiral organic group has an enantiomeric excess of at least 90 percent. In certain embodiments, the chiral organic group has an enantiomeric excess of at least 95 percent.

In certain embodiments, the chiral boronic acid has an enantiomeric excess of at least 80 percent. In certain embodiments, the chiral boronic acid has an enantiomeric excess of at least 90 percent. In certain embodiments, the chiral boronic acid has an enantiomeric excess of at least 95 percent.

DETAILED DESCRIPTION

Definitions

Figure 1:
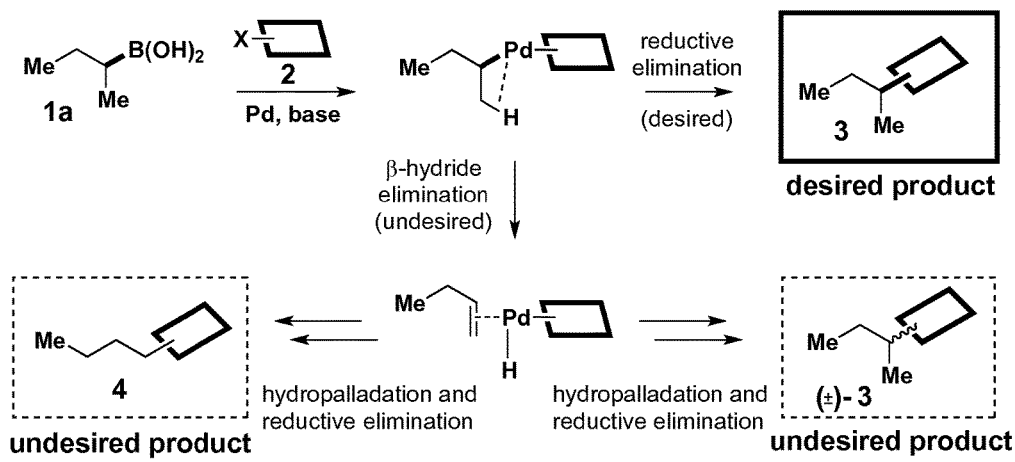
FIG. 1 depicts a scheme for preparing desired and undesired products of cross-coupling of unactivated chiral secondary boronic acids (Scheme 1).

Unless otherwise explained, all technical and scientific terms used herein have the same meaning as commonly understood by one of ordinary skill in the art to which a disclosed disclosure belongs.

For the purposes of this invention, the chemical elements are identified in accordance with the Periodic Table of the Elements, CAS version, Handbook of Chemistry and Physics, 67th Ed., 1986-1987, inside cover.

The term "acyl" or "acyl group" means any group or radical of the form —C(═O)R, where R is an organic group. An example of the acyl group is the acetyl group (—C(═O)CH$_3$).

The term "acyloxy" or "acyloxy group" as used herein refers to means an acyl group, as defined herein, appended to the parent molecular moiety through an oxygen atom.

The term "alkenyl" or "alkenyl group" means a group formed by removing a hydrogen from a carbon of an alkene, where an alkene is an acyclic or cyclic compound consisting entirely of hydrogen atoms and carbon atoms, and including at least one carbon-carbon double bond. An alkenyl group may include one or more substituent groups.

The term "alkoxy" or "alkoxy group" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkyenyloxy", "alkynyloxy", "carbocyclyloxy", and "heterocyclyloxy" are likewise defined.

The term "alkyl" or "alkyl group" means a group formed by removing a hydrogen from a carbon of an alkane, where an alkane is an acyclic or cyclic compound consisting entirely of hydrogen atoms and saturated carbon atoms. In various embodiments an alkyl contains 1 to 20, 1 to 15, or 1 to 10 carbon atoms. In one embodiment an alkyl contains 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, 1-(1-ethylcyclopropyl)ethyl and 1-cyclohexylethyl. An alkyl group may include one or more substituent groups.

The term "alkynyl group" means a group formed by removing a hydrogen from a carbon of an alkyne, where an alkyne is an acyclic or cyclic compound consisting entirely of hydrogen atoms and carbon atoms, and including at least one carbon-carbon triple bond. An alkynyl group may include one or more substituent groups.

The term "amino", "amino group", or "amine" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarbonyl, heteroaralkylcarbonyl, sufonyl, and sulfinyl groups; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "aromatic" or "aromatic group" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl" or "aryl group" means a group formed by removing a hydrogen from a ring carbon atom of an aromatic hydrocarbon. An aryl group may by monocyclic or polycyclic and may include one or more substituent groups.

The term "aryloxy" or "aryloxy group" as used herein means an aryl group, as defined herein, appended to the parent molecular moiety through an oxygen atom. The term "heteroaryloxy" or "heteroaryloxy group" as used herein means a heteroaryl group, as defined herein, appended to the parent molecular moiety through an oxygen atom. An aryloxy group may include one or more substituent groups.

The term "azido" as used herein means a —$N_3$ group.

The term "carbonyl" as used herein refers to a —C(=O)— group.

The term "chemical transform" of a substance means a product of a chemical transformation of the substance, where the product has a chemical structure different from that of the substance.

The term "chemical transformation" means the conversion of a substance into a product, irrespective of reagents or mechanisms involved.

The term "cyano" as used herein means a —C≡N group.

The term "cyclic" pertains to compounds and/or groups which have one or more rings (e.g., spiro, fused, bridged).

The term "cycloalkyl" or "cycloalkyl group" is a subset of alkyl which refers to a cyclic hydrocarbon radical containing from 3 to 15, 3 to 10, or 3 to 7 carbon atoms. Representative examples of cycloalkyl include, but are not limited to, cyclopropyl, cyclobutyl, cyclopentyl, and cyclohexyl. A cycloalkyl group may include one or more substituent groups.

The term "enantiomeric excess" (ee) means the absolute difference between the mole fraction of each enantiomer.

The term "functional group" means an atom or collection of atoms in a molecule that are responsible for characteristic chemical reactions of the molecule. Nonlimiting examples of functional groups include halogen, alcohol (—OH), aldehyde (—CH=O), ketone (—C(=O)—), carboxylic acid (—C(=O)OH), thiol (—SH), sulfone, sulfoxide, amine, phosphine, phosphite, phosphate, and combinations thereof. Of particular interest as functional groups in connection with the invention are alkenyl (olefinic) groups. Additional examples of organic groups including functional groups that may be present in a protected organoboronic acid are illustrated or described throughout the present application.

The term "group" means a linked collection of atoms or a single atom within a molecular entity, where a molecular entity is any constitutionally or isotopically distinct atom, molecule, ion, ion pair, radical, radical ion, complex, conformer, etc., identifiable as a separately distinguishable entity. The description of a group as being "formed by" a particular chemical transformation does not imply that this chemical transformation is involved in making the molecular entity that includes the group.

The term "halogen" means —F, —Cl, —Br or —I.

The term "heteroalkenyl" or "heteroalkenyl group" means a group formed by removing a hydrogen from a carbon of a heteroalkene, where a heteroalkene is an acyclic or cyclic compound consisting entirely of hydrogen atoms, carbon atoms, and one or more heteroatoms, and including at least one carbon-carbon double bond. A heteroalkenyl group may include one or more substituent groups.

The term "heteroalkyl group" means a group formed by removing a hydrogen from a carbon of a heteroalkane, where a heteroalkane is an acyclic or cyclic compound consisting entirely of hydrogen atoms, saturated carbon atoms, and one or more heteroatoms. A heteroalkyl group may include one or more substituent groups.

The term "heteroalkynyl" or "heteralkynyl group" means a group formed by removing a hydrogen from a carbon of a heteroalkyne, where a heteroalkyne is an acyclic or cyclic compound consisting entirely of hydrogen atoms, carbon atoms and one or more heteroatoms, and including at least one carbon-carbon triple bond. A heteroalkynyl group may include one or more substituent groups.

The term "heteroaralkyl", "heteroaralkyl group", "heteroarylalkyl", or "heteroarylalkyl group" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl. A heteroaralkyl group may include one or more substituent groups.

The term "heteroaromatic" or "heteroaromatic group" as used herein means an aromatic group as defined herein, in which at least one carbon atom is replaced by a heteroatom. Representative examples of heteroaromatic groups include, without limitation, pyrrolyl, furanyl, thiophenyl, imidazolyl, oxazolyl, thiazolyl, pyrazolyl, pyridinyl, pyrimidinyl, purinyl, quinolinyl, isoquinolinyl, and carbazolyl. A heteroaromatic group may include one or more substituent groups.

The term "heteroaryl" or "heteroaryl group" as used herein means a radical of aromatic ring systems, including, but not limited to, monocyclic, bicyclic and tricyclic rings, which have 3 to 12 atoms including at least one heteroatom, such as nitrogen, oxygen, or sulfur. Representative examples of heteroaryl groups include, without limitation, aminobenzimidazolyl, benzimidazolyl, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention may include one or more substituent groups.

The term "heteroatom" means any atom that is not carbon or hydrogen. In certain embodiments a heteroatom is an atom selected from any of nitrogen, oxygen, sulfur, and phosphorus.

The term "heterocyclyl", "heterocyclic", or "heterocyclic group" as used herein refers to a radical of a non-aromatic ring system, including, but not limited to, monocyclic, bicyclic and tricyclic rings, which can be completely saturated or which can contain one or more units of unsaturation, and has 3 to 12 atoms including at least one heteroatom, such as nitrogen, oxygen, or sulfur. For the avoidance of doubt, the degree of unsaturation does not result in an aromatic ring system. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention may include one or more substituent groups.

The term "heteroaryl group" means a group formed by replacing one or more methine (—C=) and/or vinylene (—CH=CH—) groups in an aryl group with a trivalent or divalent heteroatom, respectively. A heteroaryl group may by monocyclic or polycyclic and may include one or more substituent groups.

The term "hydroxyl" or "hydroxyl group" as used herein means an —OH group.

The term "organic group" means a group containing at least one carbon atom.

The term "organoboronic acid" means a compound represented by R—B(OH)$_2$, where R is an organic group that is bonded to the boron through a boron-carbon bond.

The term "phosphinyl" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH$_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

As used herein, a "polar aprotic solvent" is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

The term "protected organoboronic acid" means a chemical transform of an organoboronic acid, in which the boron has a lower chemical reactivity relative to the original organoboronic acid.

The term "silyl" as used herein includes H$_3$Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "sp$^a$ hybridization" means that an atom is bonded and/or coordinated in a configuration having a tetrahedral character of at least 50%. For tetra-coordinate boron atoms, the tetrahedral character of the boron atom is calculated by the method of Hopfl, H. (1999) *J Organomet Chem* 581:129-49. In this method, the tetrahedral character (THC) is defined as:

$$THC_{DA}(\%) = 100 \times (1 - (\Sigma_{n=1-6}|109.5 - \theta_n|°/90°))$$

where θ$_n$ is one of the six bond angles of the boron atom.

The term "substituent" or "substituent group" means a group that replaces one or more hydrogen atoms in a molecular entity. Except as may be specified otherwise, substituent groups can include, without limitation, alkyl, alkenyl, alkynyl, halo, haloalkyl, fluoroalkyl, hydroxy, alkoxy, alkyenyloxy, alkynyloxy, carbocyclyloxy, heterocyclyloxy, haloalkoxy, fluoroalkyloxy, sulfhydryl, alkylthio, haloalkylthio, fluoroalkylthio, alkyenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfony, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxyl, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, haloalkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, and silyloxy.

The term "sulfinyl" as used herein refers to a —S(=O)— group.

The term "sulfonyl" as used herein refers to a —S(=O)$_2$— group.

The term "trialkylsilyloxy" or "trialkylsilyloxy group" as used herein refers to a trialkylsilyl group, as defined herein, appended to the parent molecular moiety through an oxygen atom.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

In the claims, as well as in the specification herein, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It should also be understood that, unless clearly indicated to the contrary, in any methods claimed herein that include more than one step or act, the order of the steps or acts of the method is not necessarily limited to the order in which the steps or acts of the method are recited.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups, i.e., groups from which a proton can be removed (e.g., —COOH) or added (e.g., amines) or which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this disclosure for a given application. In specific applications, the selection of a given anion or cation for preparation of a salt may result in increased or decreased solubility of that salt.

Every formulation or combination of components described or exemplified herein can be used to practice the disclosure, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

Protected Organoboronic Acids Certain protected organoboronic acid compounds comprising a boron having an sp$^a$ hybridization, a conformationally rigid protecting group bonded to the boron, and an organic group bonded to the boron through a boron-carbon bond; methods of making same; and methods of performing chemical reactions using same are disclosed in U.S. Pat. No. 8,013,203, U.S. Pat. No. 8,318,983, and US 2013/0296573, each to Burke et al., the entire contents of which are incorporated herein by reference. Such compounds are represented generally by the following formula:

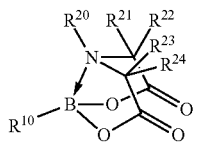

where $R^{10}$ represents the organic group, B represents the boron having sp$^3$ hybridization, and $R^{20}$, $R^{21}$, $R^{22}$, $R^{23}$, and $R^{24}$ independently are selected from the group consisting of a hydrogen group and an organic group.

In an embodiment, the protected organoboronic acid is a N-methyliminodiacetic acid (MIDA) boronate; i.e., $R^{20}$ is methyl, and each of $R^{21}$, $R^{22}$, $R^{23}$, and $R^{24}$ is hydrogen.

Protected organoboronic acids according to the foregoing formula may be prepared by reaction of an appropriate N-substituted imino-di-carboxylic acid with the corresponding unprotected boronic acid, as illustrated in the following reaction scheme:

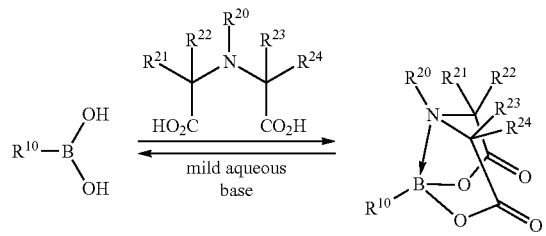

In a specific example, protected organoboronic acids according to the foregoing formula may be prepared by reaction of N-methyliminodiacetic acid (MIDA) with the corresponding unprotected boronic acid, as illustrated in the following reaction scheme:

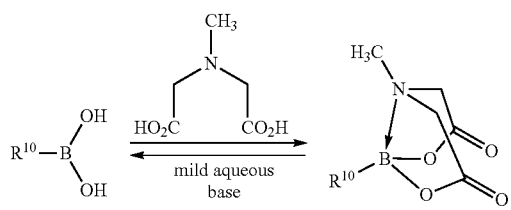

In each case, the protected organoboronic acid may be deprotected by contact with a mild aqueous base, to provide the free boronic acid.

Chiral Protected Organoboronic Acids

Certain protected organoboronic acid compounds comprising a boron having an sp$^3$ hybridization, a conformationally rigid protecting group bonded to the boron, a chiral first organic group bonded to the protecting group, and a second organic group bonded to the boron through a boron-carbon bond; methods of making same; and methods of performing chemical reactions using same are disclosed in U.S. Patent Application Publication No. 2014/0094615 to Burke et al., the entire content of which is incorporated herein by reference. Such compounds are represented generally by the following formula:

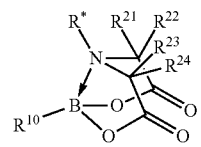

where $R^{10}$ represents the second organic group, B represents the boron having sp$^a$ hybridization, R* represents the chiral first organic group, and $R^{21}$, $R^{22}$, $R^{23}$, and $R^{24}$ independently are selected from the group consisting of a hydrogen group and an organic group.

In certain embodiments, R* is a chiral group represented by

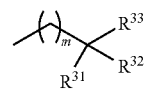

wherein:
$R^{31}$ and $R^{32}$ are independently selected from the group consisting of hydrogen, alkyl, cycloalkyl, heterocyclyl, aryl, heteroaryl, aralkyl, and heteroaralkyl; or $R^{31}$ and $R^{32}$, taken together, form a 5-10-membered cycloalkyl or aromatic ring, or form a 5-10-membered heterocyclic or heteroaromatic ring comprising 1-3 heteroatoms independently selected from the group consisting of N, O, and S;
$R^{33}$ is selected from the group consisting of hydrogen, alkyl, cycloalkyl, heterocyclyl, aryl, heteroaryl, aralkyl, and heteroaralkyl; and
m is an integer 0, 1, or 2.

In certain embodiments, R* is a chiral group of at least 90 percent enantiomeric excess.

In certain embodiments, $R^{21}$, $R^{22}$, $R^{23}$, and $R^{24}$ are independently selected from the group consisting of hydrogen and $(C_1-C_3)$alkyl.

In an embodiment, $R^1$ and $R^2$, and/or $R^3$ and $R^4$, are independently selected from the group consisting of hydrogen and $(C_1-C_3)$alkyl.

In certain embodiments, $R^{21}$, $R^{22}$, $R^{23}$, and $R^{24}$ are hydrogen.

In one embodiment, R* is

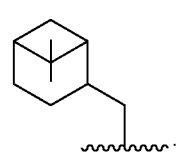

In one embodiment, R* is

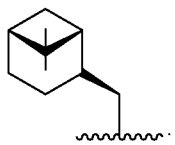

In one embodiment, R* is

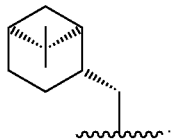

In one embodiment, R* is selected from the group consisting of

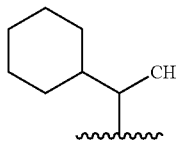 and 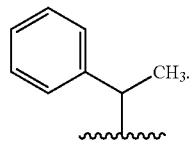

In one embodiment, R* is selected from the group consisting of

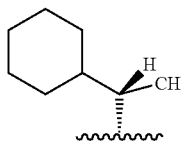 and 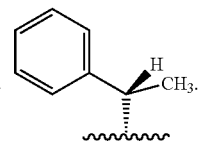

In one embodiment, R* is selected from the group consisting of

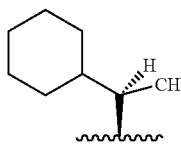 and 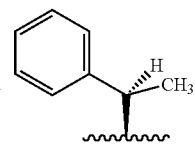

In one embodiment, $R^{31}$ and $R^{32}$, taken together, form a 5-10-membered cycloalkyl or aromatic ring, or form a 5-10-membered heterocyclic or heteroaromatic ring comprising 1-3 heteroatoms independently selected from the group consisting of N, O, and S.

In one embodiment, R* is

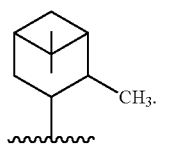 [SMILES: *C1CC2CC(C1C)C2(C)C]

In one embodiment, R* is

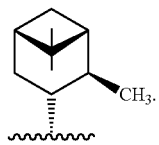

In one embodiment, R* is

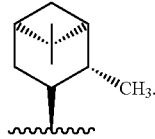

In one embodiment, R* is

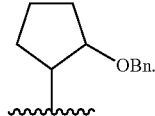

In one embodiment, R* is

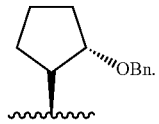

In one embodiment, R* is

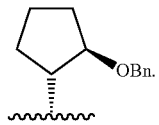

Protected chiral organoboronic acids according to the foregoing formula may be prepared by reaction of an appropriate N-substituted imino-di-carboxylic acid with the corresponding unprotected boronic acid, as illustrated in the following reaction scheme:

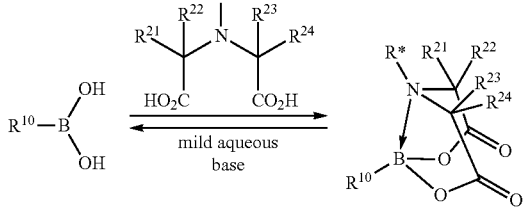

In a specific example, chiral protected organoboronic acids according to formula (I) may be prepared by reaction of N-pinene-iminodiacetic acid (PIDA) with the corresponding unprotected boronic acid (V), as illustrated in the following reaction scheme:

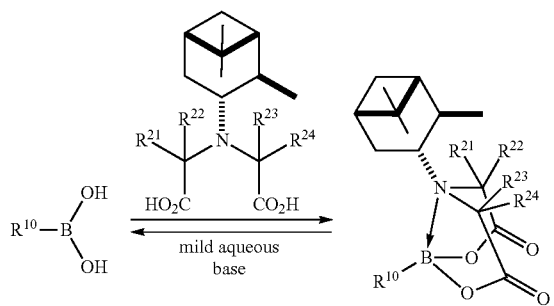

In each case, the chiral protected organoboronic acid may be deprotected by contact with a mild aqueous base, to provide the free boronic acid.

Methods of the Invention

Achieving the targeted site- and stereo-retentive cross-coupling of unactivated chiral secondary boronic acids, e.g., 1a, required concomitantly overcoming several major challenges (Scheme 1, FIG. 1), including: (i) reactivity—unactivated $Csp^3$ boronic acids are less reactive than their $Csp^2$ and activated $Csp^3$ counterparts; (ii) site-retention—a competing sequence of beta-hydride elimination followed by hydropalladation and reductive elimination from the less sterically hindered primary carbon-palladium bond typically generates undesired linear product 4 as a major byproduct; and (iii) stereo-retention—competitive retentive vs. invertive transmetalation[3d] and/or an undesired sequence of beta-hydride elimination followed by hydropalladation and reductive elimination from a secondary carbon-palladium bond may cause loss of the stereochemical information present in the starting boronic acid.

TABLE 1

Efficient and site-retentive cross-coupling of 1a.[a]

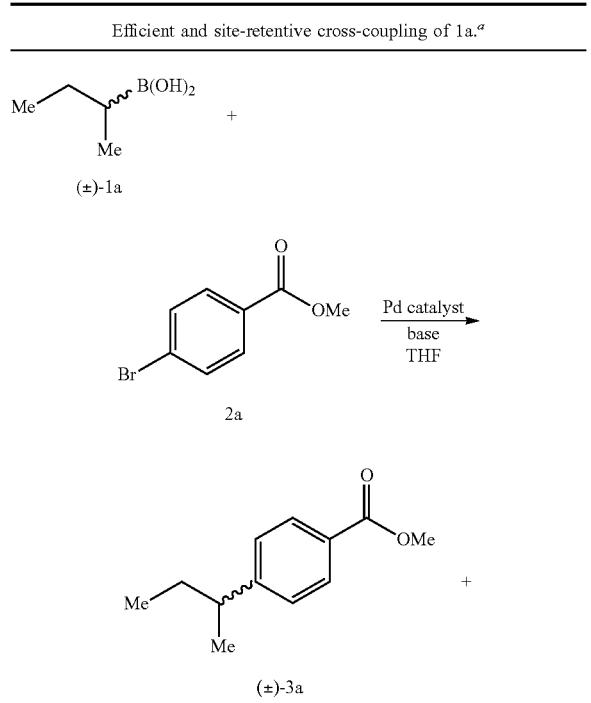

| entry | catalyst | added ligand | base | combined yield (%)[b] | 3a:4a |
|---|---|---|---|---|---|
| 1 | Pd(PPh$_3$)$_4$ | — | K$_2$CO$_3$ | 0 | — |
| 2 | Pd(PPh$_3$)$_4$ | — | K$_3$PO$_4$ | 0 | — |
| 3 | Pd(PPh$_3$)$_4$ | — | NaOH | 0 | — |
| 4 | Pd(PPh$_3$)$_4$ | — | Ag$_2$O | 81 | 1:1 |
| 5 | Pd(dCypf)Cl$_2$ | — | Ag$_2$O | 0 | — |
| 6 | Pd(dt-Bupf)Cl$_2$ | — | Ag$_2$O | 16 | 1:1 |
| 7 | Pd(dppf)Cl$_2$ | — | Ag$_2$O | 65 | 1:1 |
| 8 | Pd(OAc)$_2$ | Cy$_3$P | Ag$_2$O | 0 | — |
| 9 | Pd(OAc)$_2$ | tBu$_3$P | Ag$_2$O | 0 | — |
| 10 | Pd(OAc)$_2$ | Bu$_2$MeP | Ag$_2$O | 0 | — |
| 11 | Pd(OAc)$_2$ | SPhos | Ag$_2$O | <5 | — |
| 12 | Pd(OAc)$_2$ | XPhos | Ag$_2$O | <5 | — |
| 13 | Pd(OAc)$_2$ | Ruphos | Ag$_2$O | 0 | — |
| 14 | Pd(OAc)$_2$ | P(o-tol)$_3$ | Ag$_2$O | 47 | >20:1 |
| 15 | Pd(P(o-tol)$_3$)$_2$ | — | Ag$_2$O | 81 | >20:1 |

[a]Reaction conditions: 2 equiv. of 1, 5 equiv. of base, 10 mol % catalyst, 20 mol % added ligand, THF, 85° C., 24 h.
[b]Yields obtained by $^1$H NMR using hexamethylbenzene as an internal standard; average of two runs.

To address the first two of these problems (i.e., reactivity and site-retention), we pursued the cross-coupling of racemic unactivated secondary boronic acid (±)-1a with aryl halide 2a (Table 1). Previous reports of similar couplings involved low to moderate yields and/or undesirable branched:linear ratios.[4b-d] Consistent with the poor reactivity of secondary boronic acids, a series of standard catalyst and base combinations yielded no product (Table 1, entries 1-3). Silver(I) oxide has been shown to promote Suzuki-Miyaura reactions with primary alkyl boronic acids' and activated secondary boronic esters.[3a] We found that the combination of Pd(PPh$_3$)$_4$ and Ag$_2$O in THF promoted the reaction of 1 with 2a to generate an 86% yield of cross-coupling products, albeit as a 1:1 ratio of branched and linear isomers 3a and 4a (Table 1, entry 4).

Turning our attention to the problem of site-retention, we first tested ligand/Pd systems with the potential to accelerate the desired reductive elimination pathway. However, bidentate phosphine ligands[8] resulted in decreased yields and/or no improvement in site-selectivity (entries 5-7), and bulky trialkylphosphine ligands[4a] did not yield any detectable product (entries 8-10). We also sought to disfavor the undesired β-hydride elimination pathway by employing ligands that might block the required agostic interaction between Pd and a β-hydrogen on the alkyl ligand (Scheme 1, FIG. 1). Buchwald-type dialkyl biaryl phosphine ligands, which possess an ipso-interaction between the Pd center and the biaryl moiety on the ligand,[9] and thus could theoretically achieve this goal, are ineffective in promoting the desired cross-coupling (entries 11-13). We also noted that a mechanistically analogous but undesirable β-hydride elimination pathway that competes during C—N cross-coupling with primary alkyl amines was suppressed by the use of Pd(P(o-tol)$_3$)$_2$,[10] in which the ortho-methyl groups on the ligand may sterically block the required open coordination site on Pd. Encouragingly, the addition of Pd(OAc)$_2$ and P(o-tol)$_3$ provided a 20:1 ratio of 3a:4a, albeit in modest yield. Alternative employment of preformed Pd(P(o-tol)$_3$)$_2$,[10b] an air-stable and commercially available complex, afforded both excellent reactivity and virtually complete site-retention (entry 15).

We next set out to determine the stereochemical course of this reaction by employing the unactivated secondary boronic acid 1a in non-racemic form. To our knowledge, the stereochemical course for such a cross-coupling reaction has not been previously determined. We quickly recognized that two additional challenges have likely contributed to this lack of precedent: (i) building block access—methods are rare for accessing unfunctionalized chiral boronic acids such as 1a in non-racemic form;[11] and (ii) stability—secondary boronic acids can be quite unstable; e.g., the half-life of (±)-1 in a vial on the benchtop under air is less than 24 hours.[12]

Figure 2:
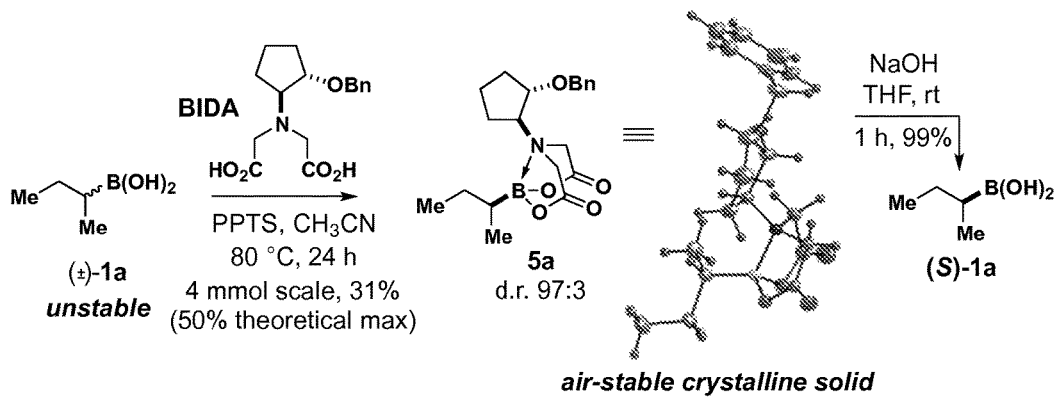
FIG. 2 depicts a scheme for stabilization of an unstable secondary boronic acid and deprotection of the stabilized secondary boronic acid (Scheme 2).
Figure 3:
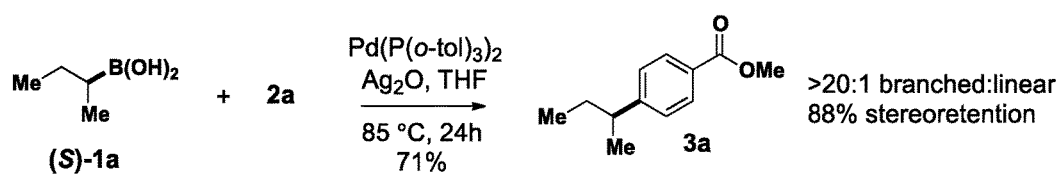
FIG. 3 depicts a scheme for cross-coupling a chiral non-racemic secondary boronic acid with high site- and stereo-retention (Scheme 3).
Figure 4:
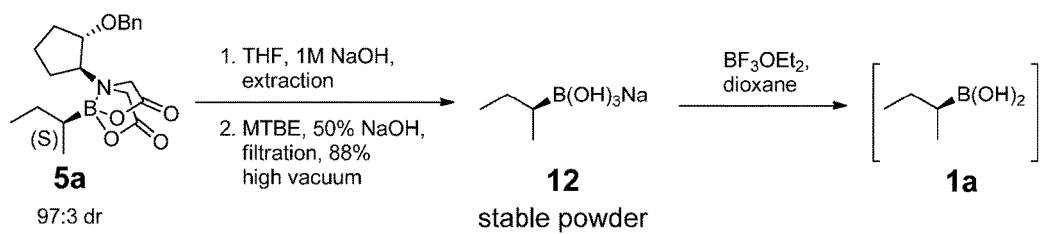
FIG. 4 depicts an exemplary series of steps for preparing a chiral nonracemic boronic acid from a diastereomerically enriched cyclic boronate via the intermediacy of a stable chiral nonracemic sodium trihydroxyborate salt. The series of steps can be applied to any of a range of cyclic boronates to produce boronic acids from cyclic boronates via the intermediacy of stable sodium trihydroxyborate salts.

Building on our recently reported chiral iminodiacetic acid ligand platform,[5j] we developed a simple and practical solution to both of these problems. Specifically, the complexation of racemic 2-butyl boronic acid (±)-1a with 2-benzyloxycyclopentyl-derived iminodiacetic acid (BIDA) using PPTS in CH$_3$CN[13] followed by trituration and recrystallization provides iminodiacetic acid boronate 5a in highly diastereomerically enriched form (97:3 d.r., Scheme 2 (FIG. 2)). Like most MIDA boronates,[5] BIDA boronate 5a is readily amenable to single crystal growth and X-ray analysis, enabling the stereochemistry at the boron-bearing carbon to be unambiguously assigned.[12a] Moreover, in stark contrast to 1a, building block 5a is stable for more than a year on the benchtop under air.[12a] It was further determined that highly pure and enantiomerically enriched (S)-1a can be prepared in nearly quantitative yield via the simple hydrolysis of 5a (Scheme 3 (FIG. 3)). This convenient new chiral building block, 5a, and the BIDA ligand will soon be commercially available.[5z]

With robust and practical access to (S)-1a, we subjected this unactivated chiral nonracemic boronic acid to our optimized cross-coupling conditions and determined the stereochemical outcome via chiral HPLC analysis and comparison of optical rotation to literature precedent 14a (Scheme 3 (FIG. 3)). The desired product 3a was formed with an excellent level of stereo-retention.

TABLE 2

Efficient, site- and stereo-retentive cross-coupling of unactivated secondary boronic acids.[a]

| entry | secondary boronic acid (1) | halide (2) | product (3) | yield (%) | b:l ratio | stereo-retention (%) |
|---|---|---|---|---|---|---|
| 1 | (S)-1a (Me-CH(Me)-B(OH)$_2$) | 2b (4-I-C$_6$H$_4$-CO$_2$Me) | 3a | 69 | >20:1 | 91 |
| 2 | (S)-1a | 2c (2-Br-naphthalene) | 3b | 84 | >20:1 | 88 |
| 3 | (S)-1a | 2d X = Br | 3c X = Br | 81 | >20:1 | 94 |
| 4 | (S)-1a | 2e X = I | 3c X = I | 83 | >20:1 | 94 |

TABLE 2-continued

Efficient, site- and stereo-retentive cross-coupling of unactivated secondary boronic acids.[a]

$$\underset{1}{\underset{R_2}{\overset{R_1}{>}}\text{B(OH)}_2} + \underset{2}{\underset{X}{\bigcirc}\text{—R}} \xrightarrow[\text{Ag}_2\text{O, THF}]{\text{Pd(P(o-tol)}_3)_2} \underset{3}{\underset{R_2}{\overset{R_1}{>}}\bigcirc\text{—R}}$$

| entry | secondary boronic acid (1) | halide (2) | product (3) | yield (%) | b:l ratio | stereo-retention (%) |
|---|---|---|---|---|---|---|
| 5 | (S)-1a | 2f (Br–C₆H₄–Ph, meta) | 3d | 82 | >20:1 | 96 |
| 6 | (S)-1a | 2g X = Br (ortho-Ph) | 3e X = Br | 0 | — | — |
| 7 | (S)-1a | 2h X = I | 3e X = I | 0 | — | — |
| 8 | (S)-1a | 2i X = Br (para-t-Bu) | 3f X = Br | 31 | >20:1 | n.d. |
| 9 | (S)-1a | 2j X = I | 3f X = I | 61 | >20:1 | n.d. |
| 10 | 1b (cyclopropyl-B(OH)₂) | 2a | 3g | 95 | — | — |
| 11 | 1c (cyclobutyl-B(OH)₂) | 2a | 3h | 95 | — | — |
| 12 | 1d (cyclopentyl-B(OH)₂) | 2a | 3i | 76 | — | — |

TABLE 2-continued

Efficient, site- and stereo-retentive cross-coupling of unactivated secondary boronic acids.[a]

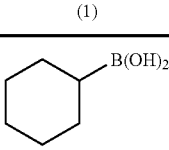

| entry | secondary boronic acid (1) | halide (2) | product (3) | yield (%) | b:l ratio | stereo-retention (%) |
|---|---|---|---|---|---|---|
| 13 | 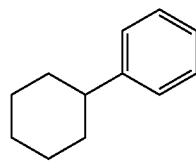 1e | 2a | 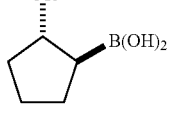 3j | 69 | — | — |
| 14 | 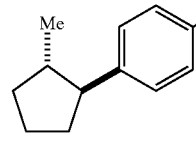 (±)-1f | 2a | 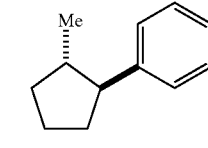 (±)-3k | 66 | n.d. | — |
| 15 | (±)-1f | 2e | 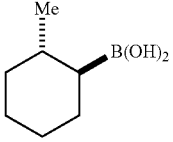 (±)-3l | 70 | n.d. | — |
| 16 | 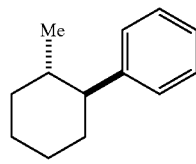 (±)-1g | 2a | 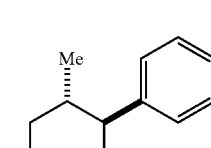 (±)-3m | 65 | n.d. | — |
| 17 | (±)-1g | 2e | (±)-3n | 62 | n.d. | — |
| 18 | (±)-1f | 2a | (±)-3k | 54 | n.d. | 99 |

[a]Reaction conditions: 0.2 mmol of 1, 0.1 mmol of 3, 0.5 mmol of Ag$_2$O, 0.01 mmol of Pd(P(o-tol)$_3$)$_2$, THF, 85° C., 24 h. The absolute stereochemistry of 3a and 3b were determined by comparison of optical rotation to the corresponding literature values.[14] The absolute stereochemistry of 3c-f were assigned by analogy.
b:l ratio = branched:linear ratio.
n.d. = not determined.

We then completed a survey of the reaction scope (Table 2). Chiral nonracemic unactivated secondary boronic acid (S)-1a was coupled to both activated and non-activated aryl bromides and iodides (entries 1-5), with excellent to outstanding branched:linear ratios and stereo-retention. Electronic deactivation of the aryl halide is tolerated, as cross-coupling was achieved with para-t-butylbromobenzene 2i (entry 8) and even more effectively with the corresponding iodide 2j (entry 9). We found that a range of different cyclic secondary boronic acids are also excellent substrates (entries 10-17). Importantly, there is tolerance to increased steric bulk on the secondary boronic acid coupling partner, with anti-1-methyl-2-cyclopentylboronic acid (10 and anti-1-methyl-2-cyclohexylboronic acid (1g)[16a] reacting with activated and unactivated halides to yield the corresponding cross-coupling products 3k-3n in good yields (entries 14-17). Finally, outstanding retention of stereochemical purity is maintained when boronic acid 1f is employed in nonracemic form (entry 18).[16b]

An aspect of the invention is a method of forming a product represented by $R^1R^2CH$-Ar, comprising:

combining a secondary boronic acid represented by $R^1R^2CH$—$B(OH)_2$; an aryl halide represented by Ar-X; a Pd catalyst; a ligand; and $Ag_2O$:

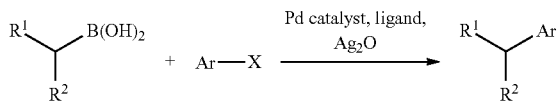

wherein, independently for each occurrence, $R^1$ and $R^2$ are selected from the group consisting of substituted $C_1$-$C_6$ alkyl and unsubstituted $C_1$-$C_6$ alkyl; or $R^1$ and $R^2$, taken together with the carbon to which they are joined, form a substituted or unsubstituted $C_3$-$C_8$ cycloalkyl;

Ar represents a substituted or unsubstituted monocyclic or polycyclic aryl;

X represents halogen;

Pd catalyst represents Pd(0) or Pd(II);

ligand is $P(o\text{-R-phenyl})_3$; and

R represents $C_1$-$C_4$ alkyl;

thereby forming a product represented by $R^1R^2CH$-Ar.

In certain embodiments, Pd catalyst represents Pd(0).

In certain embodiments, Pd catalyst represents Pd(II).

In certain embodiments, ligand is $P(o\text{-tol})_3$ (i.e., R is methyl).

In certain embodiments, the secondary boronic acid is achiral.

In certain embodiments, the secondary boronic acid is chiral.

In certain embodiments, the secondary boronic acid is a racemic mixture.

In certain embodiments, the secondary boronic acid is not a racemic mixture. The phrase "is not a racemic mixture" as used herein shall be understood to be equivalent to the phrase "is a non-racemic mixture".

In certain embodiments, the secondary boronic acid has an enantiomeric excess of at least 80 percent. That is, in various individual embodiments, the secondary boronic acid has an enantiomeric excess of at least 80 percent, at least 81 percent, at least 82 percent, at least 83 percent, at least 84 percent, at least 85 percent, at least 86 percent, at least 87 percent, at least 88 percent, at least 89 percent, at least 90 percent, at least 91 percent, at least 92 percent, at least 93 percent, at least 94 percent, at least 95 percent, at least 96 percent, at least 97 percent, at least 98 percent, or at least 99 percent. In certain embodiments, the secondary boronic acid has an enantiomeric excess of at least 90 percent.

In certain embodiments, the secondary boronic acid has an enantiomeric excess of at least 95 percent.

In certain embodiments, the product represented by $R^1R^2CH$—Ar is not a racemic mixture.

In certain embodiments, the product represented by $R^1R^2CH$-Ar has an enantiomeric excess of at least 80 percent.

In certain embodiments, the product represented by $R^1R^2CH$-Ar has an enantiomeric excess of at least 90 percent.

In certain embodiments, the product represented by $R^1R^2CH$-Ar has an enantiomeric excess of at least 95 percent.

In certain embodiments, $R^1$ and $R^2$ are selected from the group consisting of substituted $C_1$-$C_6$ alkyl and unsubstituted $C_1$-$C_6$ alkyl.

In certain embodiments, $R^1$ and $R^2$, taken together with the carbon to which they are joined, form a substituted or unsubstituted $C_3$-$C_8$ cycloalkyl.

In certain embodiments, Ar represents a substituted or unsubstituted phenyl.

In certain embodiments, Ar represents a substituted or unsubstituted polycyclic aryl.

In certain embodiments, X is Br.

In certain embodiments, X is I.

An aspect of the invention is a method of forming an air-stable chiral secondary boronic acid, wherein the air-stable chiral secondary boronic acid is not a racemic mixture, comprising:

combining a chiral secondary boronic acid represented by formula (I)

wherein, independently for each occurrence, $R^1$ and $R^2$ are selected from the group consisting of substituted $C_1$-$C_6$ alkyl and unsubstituted $C_1$-$C_6$ alkyl; a chiral iminodiacetic acid, wherein the chiral iminodiacetic acid is not a racemic mixture; a weak acid catalyst; and a polar aprotic solvent, thereby forming a mixture of chiral boronates;

resolving the mixture of chiral boronates into individual diastereomers; and hydrolyzing an individual diastereomer, thereby forming an air-stable chiral secondary boronic acid, wherein the air-stable chiral secondary boronic acid is not a racemic mixture.

In certain embodiments, the resolving is by crystallization.

In certain embodiments, the resolving is by chromatography.

In certain embodiments, the hydrolyzing is with aqueous hydroxide.

In certain embodiments, the hydrolyzing is with aqueous NaOH.

In certain embodiments, the chiral iminodiacetic acid has an enantiomeric excess of at least 80 percent. That is, in various individual embodiments, the chiral iminodiacetic acid has an enantiomeric excess of at least 80 percent, at least 81 percent, at least 82 percent, at least 83 percent, at least 84 percent, at least 85 percent, at least 86 percent, at least 87 percent, at least 88 percent, at least 89 percent, at least 90 percent, at least 91 percent, at least 92 percent, at least 93 percent, at least 94 percent, at least 95 percent, at least 96 percent, at least 97 percent, at least 98 percent, or at least 99 percent.

In certain embodiments, the chiral iminodiacetic acid has an enantiomeric excess of at least 90 percent.

In certain embodiments, the chiral iminodiacetic acid has an enantiomeric excess of at least 95 percent.

In certain embodiments, the chiral iminodiacetic acid is benzylcyclopentyl iminodiacetic acid (BIDA).

In certain embodiments, the weak acid catalyst is pyridinium p-toluenesulfonate (PPTS).

In certain embodiments, the polar aprotic solvent is $CH_3CN$.

In certain embodiments, the chiral secondary boronic acid represented by formula (I) is a racemic mixture.

In certain embodiments, the chiral secondary boronic acid represented by formula (I) is not a racemic mixture.

In certain embodiments, the air-stable chiral secondary boronic acid has an enantiomeric excess of at least 80 percent. That is, in various individual embodiments, the air-stable chiral secondary boronic acid has an enantiomeric excess of at least 80 percent, at least 81 percent, at least 82 percent, at least 83 percent, at least 84 percent, at least 85 percent, at least 86 percent, at least 87 percent, at least 88 percent, at least 89 percent, at least 90 percent, at least 91 percent, at least 92 percent, at least 93 percent, at least 94 percent, at least 95 percent, at least 96 percent, at least 97 percent, at least 98 percent, or at least 99 percent.

In certain embodiments, the air-stable chiral secondary boronic acid has an enantiomeric excess of at least 90 percent.

In certain embodiments, the air-stable chiral secondary boronic acid has an enantiomeric excess of at least 95 percent.

An aspect of the invention is a method of forming an air-stable trihydroxyborate salt of a primary or secondary boronic acid, comprising:

(i) combining a primary or secondary boronate represented by formula (II):

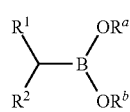

(II)

a first polar aprotic solvent, and aqueous hydroxide, thereby forming a primary or secondary boronic acid represented by formula (I):

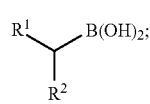

(I)

wherein, independently for each occurrence, $R^1$ is selected from the group consisting of substituted $C_1$-$C_6$ alkyl and unsubstituted $C_1$-$C_6$ alkyl;

$R^2$ is selected from the group consisting of H, substituted $C_1$-$C_6$ alkyl and unsubstituted $C_1$-$C_6$ alkyl; and $R^a$ and $R^b$ are selected from the group consisting of optionally substituted alkyl, aryl, and acyl; or $R^a$ and $R^b$ taken together with the —O—B(CHR$^1$R$^2$)—O— moiety to which they are attached form an optionally substituted heterocyclic ring consisting of 5-10 heavy atoms in the backbone of said heterocyclic ring, wherein 3-5 heteroatoms selected independently from the group consisting of B, O, and N are present in said heterocyclic ring; and (ii) combining the primary or secondary boronic acid represented by formula (I), an ether, and concentrated hydroxide, thereby forming an air-stable trihydroxyborate salt of a primary or secondary boronic acid.

In certain embodiments, the method further comprises combining the air-stable trihydroxyborate salt of a primary or secondary boronic acid, a Lewis acid, and a second polar aprotic solvent, thereby re-forming the primary or secondary boronic acid represented by formula (I).

In certain embodiments, the Lewis acid is $BF_3OEt_2$.

In certain embodiments, the second polar aprotic solvent is dioxane.

In certain embodiments, the primary or secondary boronate represented by formula (II) is represented by formula (III):

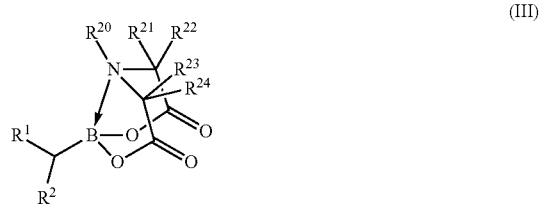

(III)

wherein, independently for each occurrence, $R^1$ is selected from the group consisting of substituted $C_1$-$C_6$ alkyl, and unsubstituted $C_1$-$C_6$ alkyl;

$R^2$ is selected from the group consisting of H, substituted $C_1$-$C_6$ alkyl, and unsubstituted $C_1$-$C_6$ alkyl;

B represents boron having $sp^a$ hybridization; and $R^{20}$, $R^{21}$, $R^{22}$, $R^{23}$, and $R^{24}$ independently are selected from the group consisting of a hydrogen group and an organic group.

In certain embodiments, $R^{21}$, $R^{22}$, $R^{23}$, and $R^{24}$ each represent a hydrogen group.

In certain embodiments, the primary or secondary boronate represented by formula (II) is achiral.

In certain embodiments, the primary or secondary boronic acid represented by formula (I) is a primary boronic acid.

In certain embodiments, the primary or secondary boronic acid represented by formula (I) is a secondary boronic acid.

In certain embodiments, the air-stable salt of the primary or secondary boronic acid is achiral.

In certain embodiments, the primary or secondary boronate represented by formula (II) is chiral.

In certain embodiments, the primary or secondary boronate represented by formula (II) is represented by formula (IV):

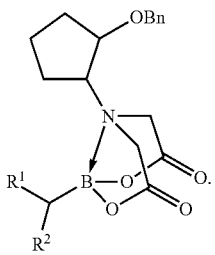

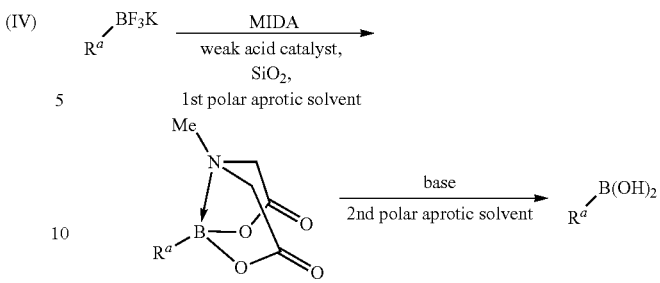

In certain embodiments, the primary or secondary boronic acid represented by formula (I) is a primary boronic acid.

In certain embodiments, the primary or secondary boronic acid represented by formula (I) is a secondary boronic acid.

In certain embodiments, the secondary boronic acid is achiral.

In certain embodiments, the secondary boronic acid is chiral.

In certain embodiments, the chiral secondary boronic acid represented by formula (I) is a racemic mixture.

In certain embodiments, the chiral secondary boronic acid represented by formula (I) is not a racemic mixture.

In certain embodiments, the chiral primary or secondary boronate represented by formula (II) is a racemic mixture.

In certain embodiments, the chiral primary or secondary boronate represented by formula (II) is not a racemic mixture.

In certain embodiments, the chiral primary or secondary boronate represented by formula (II) has an enantiomeric excess of at least 80 percent.

In certain embodiments, the chiral primary or secondary boronate represented by formula (II) has an enantiomeric excess of at least 90 percent.

In certain embodiments, the chiral primary or secondary boronate represented by formula (II) has an enantiomeric excess of at least 95 percent.

In certain embodiments, the air-stable salt of the primary or secondary boronic acid is a chiral air-stable salt of the secondary boronic acid.

In certain embodiments, the chiral air-stable salt of the secondary boronic acid is a racemic mixture.

In certain embodiments, the chiral air-stable salt of the secondary boronic acid is not a racemic mixture.

In certain embodiments, the chiral air-stable salt of the secondary boronic acid has an enantiomeric excess of at least 80 percent.

In certain embodiments, the chiral air-stable salt of the secondary boronic acid has an enantiomeric excess of at least 90 percent.

In certain embodiments, the chiral air-stable salt of the secondary boronic acid has an enantiomeric excess of at least 95 percent.

In certain embodiments, the first polar aprotic solvent is tetrahydrofuran (THF).

In certain embodiments, the aqueous hydroxide is aqueous NaOH.

In certain embodiments, the ether is methyl tert-butyl ether (MTBE).

In certain embodiments, the concentrated hydroxide is concentrated NaOH.

An aspect of the invention is a method of forming a boronic acid, comprising the steps represented by:

wherein $R^a$ represents an organic group; and

MIDA represents N-methyliminodiacetic acid.

In certain embodiments, the weak acid catalyst is pyridinium p-toluenesulfonate (PPTS).

In certain embodiments, the first polar aprotic solvent and the second polar aprotic solvent are the same.

In certain embodiments, the first polar aprotic solvent is $CH_3CN$.

In certain embodiments, the base is NaOH.

In certain embodiments, the second polar aprotic solvent is tetrahydrofuran (THF).

In certain embodiments, the first polar aprotic solvent is $CH_3CN$, and the second polar aprotic solvent is THF.

In certain embodiments, the organic group is a chiral organic group; and the boronic acid

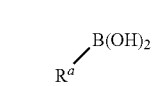

is a chiral boronic acid.

In certain embodiments, the chiral organic group is a racemic mixture; and the chiral boronic acid is a racemic mixture.

In certain embodiments, the chiral organic group is not a racemic mixture; and the chiral boronic acid is not a racemic mixture.

In certain embodiments, the chiral organic group has an enantiomeric excess of at least 80 percent. That is, in various individual embodiments, the chiral organic group has an enantiomeric excess of at least 80 percent, at least 81 percent, at least 82 percent, at least 83 percent, at least 84 percent, at least 85 percent, at least 86 percent, at least 87 percent, at least 88 percent, at least 89 percent, at least 90 percent, at least 91 percent, at least 92 percent, at least 93 percent, at least 94 percent, at least 95 percent, at least 96 percent, at least 97 percent, at least 98 percent, or at least 99 percent.

In certain embodiments, the chiral organic group has an enantiomeric excess of at least 90 percent.

In certain embodiments, the chiral organic group has an enantiomeric excess of at least 95 percent.

In certain embodiments, the chiral boronic acid has an enantiomeric excess of at least 80 percent. That is, in various individual embodiments, the chiral boronic acid has an enantiomeric excess of at least 80 percent, at least 81 percent, at least 82 percent, at least 83 percent, at least 84 percent, at least 85 percent, at least 86 percent, at least 87 percent, at least 88 percent, at least 89 percent, at least 90 percent, at least 91 percent, at least 92 percent, at least 93 percent, at least 94 percent, at least 95 percent, at least 96 percent, at least 97 percent, at least 98 percent, or at least 99 percent.

In certain embodiments, the chiral boronic acid has an enantiomeric excess of at least 90 percent.

In certain embodiments, the chiral boronic acid has an enantiomeric excess of at least 95 percent.

REFERENCES (1) (a) Merrifield, R. B. *Science* 1965, 150, 178-185. (b) Caruthers, M. H. *Science* 1985, 230, 281-285. (c) Plante, O. J.; Palmacci, E. R.; Seeberger, P. H. *Science* 2001, 291, 1523-1527.

(2) (a) Metal-Catalyzed Cross-Coupling Reactions; Diederich, F., Stang, P. J., Eds.; Wiley-VCH: Weinheim, Germany, 1998; (b) Suzuki, A.; Brown, H. C. *Organic Synthesis via Boranes*; Aldrich: Milwaukee, Wis., 2003. (c) Netherton, M. R.; Fu, G. C. In *Topics in Organometallic Chemistry: Palladium in Organic Synthesis*; Tsuji, J., Ed.; Springer: New York, 2005. (d) Glorius, F. *Angew. Chem., Int. Ed.* 2008, 47, 8347-8349. (e) Glasspoole, B. W.; Crudden, C. M. *Nat. Chem.* 2011, 3, 912-913. (f) Heravi, M. M.; Hashemi, E. *Tetrahedron* 2012, 68, 9145-9178. (g) Han, F S. *Chem. Soc. Rev.* 2013, 42, 5270-98.

(3) Recent advances in site- and/or stereo-retentive cross-coupling of activated secondary Csp$^3$ organoboronates: (a) Imao, D.; Glasspoole, B. W.; Laberge, V. S.; Crudden, C. M. *J. Am. Chem. Soc.* 2009, 131, 5024-5025. (b) Sandrock, D. L.; Jean-Gérard, L.; Chen, C.; Dreher, S. D., Molander. G. A. *J. Am. Chem. Soc.*, 2010, 132, 17108-17110. (c) Ohmura, T.; Awano, T.; Suginome, M. *J. Am. Chem. Soc.*, 2010, 132, 13191-13193. (d) Awano, T.; Ohmura, T.; Suginome, M. *J. Am. Chem. Soc.* 2011, 133, 20738-20741. (e) Daini, M.; Suginome, M. *J. Am. Chem. Soc.* 2011, 133, 4758-4761. (f) Molander, G. A.; Wisniewski, S. R. *J. Am. Chem. Soc.* 2012, 134, 16856-16868.

(4) Examples of cross-coupling of unactivated Csp$^3$ organoboronates without site- and/or stereocontrol: (a) Fu, *J. Am. Chem. Soc.* 2000, 122, 4020-4028. (b) Kataoka, N.; Shelby, Q.; Stambuli, J. P.; Hartwig, J. F. *J. Org. Chem.* 2002, 67, 5553-5566. (c) Dreher, S. D.; Dormer, P. G.; Sandrock, D. L.; Molander, G. A. *J. Am. Chem. Soc.* 2008, 130, 9257-9259. (d) van den Hoogenband, A.; Lange, J. H. M.; Terpstra, J. W.; Koch, M.; Visser, G. M.; Visser, M.; Korstanje, T. J.; Jastrzebski, J. T. B. H. *Tet. Lett.* 2008, 49, 4122-4124.

(5) (a) Gillis, E. P.; Burke, M. D. *Aldrichimica Acta* 2009, 42, 17-27. (b) Wang, C.; Glorius, F. *Angew. Chem., Int. Ed.* 2009, 48, 5240-5244. (c) Gillis, E. P.; Burke, M. D. *J. Am. Chem. Soc.* 2007, 129, 6716-6717. (d) Gillis, E. P.; Burke, M. D. *J. Am. Chem. Soc.* 2008, 130, 14084-14085. (e) Suk, J. L.; Gray, K. C.; Paek, J. S.; Burke, M. D. *J. Am. Chem. Soc.* 2008, 130, 466-468. (f) Knapp, D. M.; Gillis, E. P.; Burke, M. D. *J. Am. Chem. Soc.* 2009, 131, 6961-6963. (g) Lee, S. J.; Anderson, T. M.; Burke, M. D. *Angew. Chem., Int. Ed.* 2010, 49, 8860-8863. (h) Woerly, E. M.; Cherney, A. H.; Davis, E. K.; Burke, M. D. *J. Am. Chem. Soc.* 2010, 132, 6941-6943. (i) Fujii, S.; Chang, S. Y.; Burke, M. D. *Angew. Chem., Int. Ed.* 2011, 50, 7862-7864. (j) Li, J.; Burke, M. D. *J. Am. Chem. Soc.* 2011, 133, 13774-13777. (k) Dick, G. R.; Woerly, E. M.; Burke, M. D. *Angew. Chem., Int. Ed.* 2012, 51, 2667-2672. (l) Gray, K. C.; Palacios, D. S.; Dailey, I.; Endo, M. M.; Uno, B. E.; Wilcock, B. C.; Burke, M. D. *Proc. Natl. Acad. Sci.* 2012, 109, 2234-2239. (m) Fujita, K.; Matsui, R.; Suzuki, T.; Kobayashi, S. *Angew. Chem., Int. Ed.* 2012, 51, 7271-7274. (n) Grob, J. E.; Dechantsreiter, M. A.; Tichkule, R. B.; Connolly, M. K.; Honda, A.; Tomlinson, R. C.; Hamann, L. G. *Org. Lett.* 2012, 14, 5578-5581. (o) Grob, J. E.; Nunez, J.; Dechantsreiter, M. A.; Hamann, L. G. *J. Org. Chem.* 2011, 76, 10241-10248. (p) Grob, J. E.; Nunez, J.; Dechantsreiter, M. A.; Hamann, L. G. *J. Org. Chem.* 2011, 76, 4930-4940. (q) Dennis, E. G.; Jeffery, D. W.; Johnston, M. R.; Perkins, M. V.; Smith, P. A. *Tetrahedron* 2012, 68, 340-348. (r) He, Z.; Yudin A. K. *J. Am. Chem. Soc.* 2011, 133, 13770-13773. (s) Zhi, H.; Piera, T.; Shinya, A.; Jeffrey, D. S. D.; Yudin, A. K. *Angew. Chem., Int. Ed.* 2012, 51, 11092-11096. (t) Wang, H.; Grohmann, C.; Nimphius, C.; Glorius, F. *J. Am. Chem. Soc.* 2012, 134, 19592-19595. (u) Delaunay, T.; Es-Sayed, M.; Vors, J.; Monteiro, N.; Balme, G. *Chem. Lett.* 2011, 40, 1434-1436. (v) Chan, J. M. W.; Amarante, G. W; Toste, F. D. *Tetrahedron* 2011, 67, 4306-4312. (w) Mohamed, Y. M. A.; Trond, V. H. *Tet. Lett.* 2011, 52, 1057-1059. (x) Brak, K.; Ellman, J. A. *Org. Lett.* 2010, 12, 2004-2007. (y) Willwacher, J.; Kausch-Busies, N.; Fürstner, A. *Angew. Chem., Int. Ed.* 2012, 51, 12041-12046. (z) >140 MIDA boronates are now commercially available from Sigma-Aldrich, St. Louis, Mo.

(6) Lovering, F.; Bikker, J.; Humblet, C. *J. Med. Chem.* 2009, 52, 6752-6756.

(7) (a) Falck, J. R.; Kumar, P. S.; Reddy, Y. K.; Zou, G.; Capdevila, J. H. *Tet. Lett.* 2001, 42, 7211-7212. (b) Zou, G.; Reddy, Y. K.; Falck, J. R. *Tet. Lett.* 2001, 42, 7213-7215. (c) Barfoot, C. W.; Harvey, J. E.; Kenworthy, M. N.; Kilburn, J. P.; Ahmed, M.; Taylor, R. J. K. *Tetrahedron* 2005, 61, 3403-3417. (d) For an early report on the promoting effect of $Ag_2O$ on Suzuki-Miyaura cross-coupling, see: Uenishi, J.; Beau, J. M.; Armstrong, R. W.; Kishi, Y. *J. Am. Chem. Soc.* 1987, 109, 4756-4758.

(8) Miyaura, N.; Ishiyama, T.; Ishikawa, M.; Suzuki, A. *Tet. Lett.* 1986, 27, 6369-6372.

(9) Martin, R.; Buchwald, S. L. *Acc. Chem. Res.* 2008, 41, 1461-1473.

(10) (a) Hartwig, J. F.; Richards, S.; Baranano, D.; Paul, F. *J. Am. Chem. Soc.* 1996, 118, 3626-3633. (b) Paul, F.; Patt, J.; Hartwig, J. F. *J. Am. Chem. Soc.* 1994, 116, 5969-5970.

(11) Brown, H. C.; Jadhav, P. K.; Desai, M. C. *J. Am. Chem. Soc.* 1982, 104, 4303-4304.

(12) Commercial (+/−)-1 was shipped in a sealed vial under argon.

(13) (a) Initial attempts to resolve 1a using our previously reported PIDA ligand 5j were not successful. (b) These convenient reaction conditions (PPTS, $CH_3CN$, 80° C.) also readily promote synthesis of MIDA boronates from the corresponding boronic acids. (c) During the preparation of this manuscript, a related resolution of racemic 1,1'-bi-2-naphthol boronic acid was reported: Lee, C.; Cheon, C. *J. Org. Chem.* 2013, 78, 7086-7092. (d) For an earlier report on enantioenrichment of boronic acids with chiral ligands, see: Brown, H. C.; Gupta, A. K. *J. Organomet. Chem.* 1988, 341, 73-81.

(14) The absolute stereochemistry of 3a and 3b were determined by comparison of the optical rotation to the corresponding literature values: (a) Menicagli, R., Piccolo, O. *J. Org. Chem.* 1980, 45, 2581-2585. (b) Piccolo, O.; Menicagli, R.; Lardicci, L. *Tetrahedron* 1979, 35, 1751-1578. (c) Taylor, B. L. H.; Swift, E. C.; Waetzig, J. D.; Jarvo, E. R. *J. Am. Chem. Soc.* 2011, 133, 389-391.

(15) Molander, G. A.; Cavalcanti, L. N.; Canturk, B.; Pan, P.; Kennedy, L. E. *J. Org. Chem.* 2009, 74, 7364-7369.

(16) (a) Enabling fresh preparation of these boronic acids in excellent purity, we developed a novel method for direct transformation of trifluoroborate salts into the corresponding MIDA boronates, which in turn can be very efficiently hydrolyzed into the readily isolable corresponding boronic acids just prior to use in a reaction. Specifically, racemic 1f and 1g were prepared via direct transformation of commercially available trifluoroborate salts 6a and 6b into the corresponding MIDA boronates 7a and 7b. These air- and chromatographically stable crystalline solids were then readily hydrolyzed to the corresponding boronic acids 1f and 1g prior to the cross-coupling reactions reported in Table 2.

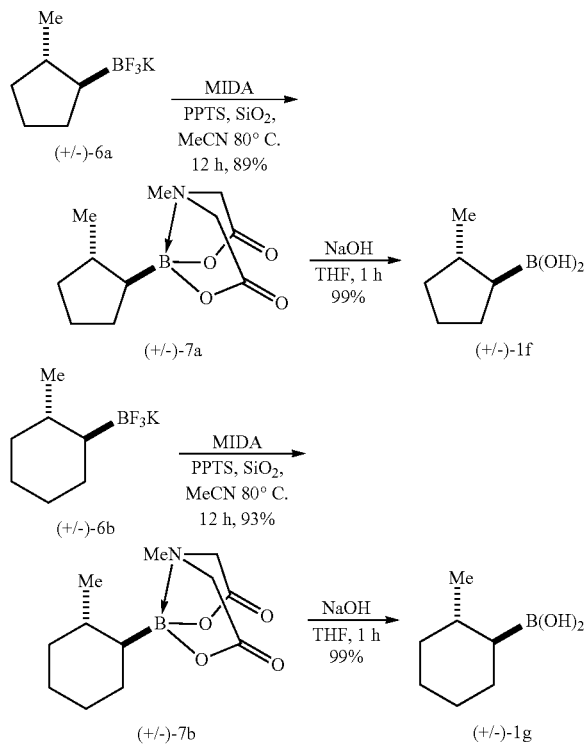

(b) This methodology was extended using the BIDA ligand to prepare boronic acid (+)-1f in highly enantiomerically enriched form (see Example 14).

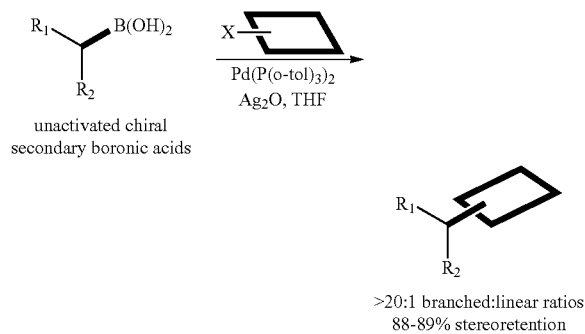

EXAMPLES

The disclosure may be further understood by the following non-limiting examples. Although the description herein contains many specific values, these should not be construed as limiting the scope of the disclosure, but as providing illustrations of some of the embodiments of the disclosure. The scope of the disclosure should be determined by the appended claims and their equivalents, rather than by the examples given.

I. General Methods

Materials.

Commercial reagents were purchased from Sigma-Aldrich, Fisher Scientific, Alfa Aesar, TCI America, or Frontier Scientific, and were used without further purification unless otherwise noted.

$Pd(P(o-tol)_3)_2$ and $Ag_2O$ were purchased from Sigma-Aldrich. A gift of $Pd(P(o-tol)_3)_2$ was donated by Johnson Matthey. Solvents were purified via passage through packed columns as described by Pangborn and coworkers[1] (THF, $Et_2O$, $CH_3CN$, $CH_2Cl_2$: dry neutral alumina; hexane, benzene, and toluene, dry neutral alumina and Q5 reactant; DMSO, DMF: activated molecular sieves). All water was deionized prior to use. Diisopropylethylamine was freshly distilled under an atmosphere of nitrogen from $CaH_2$.

General Experimental Procedures.

Unless otherwise noted, all reactions were performed in flame-dried round bottom or modified Schlenk flasks fitted with rubber septa under a positive pressure of argon or nitrogen. Organic solutions were concentrated via rotary evaporation under reduced pressure with a bath temperature of 23° C. unless otherwise noted. Reactions were monitored by analytical thin layer chromatography (TLC) performed using the indicated solvent on E. Merck silica gel 60 F254 plates (0.25 mm). Compounds were visualized by exposure to a UV lamp ($\lambda$=254 nm), and/or a solution of $KMnO_4$ and/or a solution of p-anisaldehyde, followed by brief heating using a Varitemp heat gun. Column chromatography was performed using Merck silica gel grade 9385 60 Å (230-400 mesh).

Structural Analysis.

$^1H$ NMR and $^{13}C$ NMR spectra were recorded at 20° C. on Varian Unity 500, Varian Unity Inova 500NB, or Varian Unity 500 instruments. Chemical shifts ($\delta$) are reported in parts per million (ppm) downfield from tetramethylsilane and referenced to residual protium in the NMR solvent (benzene, $\delta$=7.16; $CHCl_3$, $\delta$=7.26; acetone, $\delta$=2.05, center line; DMSO $\delta$=2.50, center line) or to added tetramethylsilane ($\delta$=0.00). Data are reported as follows: chemical shift, multiplicity (s=singlet, d=doublet, t=triplet, q=quartet, quint=quintet, sept=septet, m=multiplet, b=broad, app=apparent), coupling constant (J) in Hertz (Hz), and integration. Chemical shifts ($\delta$) for $^{13}C$ NMR are reported in ppm downfield from tetramethylsilane and referenced to carbon resonances in the NMR solvent (benzene-d6, $\delta$=128.06, center line; $CDCl_3$, $\delta$=77.0, center line; acetone-d6, $\delta$=39.5, center line; DMSO-d6 $\delta$=39.52, center line). Carbons bearing boron substituents were not observed (quadrupolar relaxation). High resolution mass spectra (HRMS) were performed by Furong Sun, Elizabeth Eves and Dr. Haijun Yao at the University of Illinois School of Chemical Sciences Mass Spectrometry Laboratory.

II. Experimental Procedures a. Synthesis of Chiral Racemic MIDA Boronates and Boronic Acids

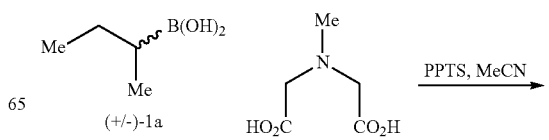

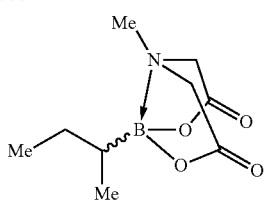

To a 40-mL sealed I-Chem vial under nitrogen was added racemic 2-butyl boronic acid (+/−)-1a (710 mg, 5 mmol), N-methyliminodiacetic acid (MIDA) (2.20 g, 15 mmol), pyridinium p-toluenesulfonate (126 mg, 0.5 mmol) followed by acetonitrile (16.7 mL, 0.3 M for the borate). The reaction was sealed and allowed to stir at 80° C. for 12 hours. After cooling down, the mixture was passed through a pad of silica gel before concentration. The light brown solid mixture was then loaded onto a silica gel column and flushed with copious amount of $Et_2O$, the product was then eluted with straight EtOAc. Upon concentration, the product was obtained as a crystalline white solid (949 mg, 89%).

$^1$H NMR (500 MHz, DMSO) δ 4.18 (d, J=17.0, 1H), 4.16 (d, J=17.0, 1H), 3.98 (d, J=17.0, 2H), 2.87 (s, 3H), 1.47 (m, 1H), 1.03 (m, 1H), 0.88 (t, J=7.5, 3H), 0.81 (d, J=7.0, 3H), 0.67 (s, 1H).

$^{13}$C NMR (126 MHz, DMSO) δ 169.1, 169.0, 62.3, 62.1, 45.4, 24.5, 13.8, 12.7.

HRMS (ESI+)

Calculated for $C_9H_{17}BNO_4$: 214.1251.

Found: 214.1252.

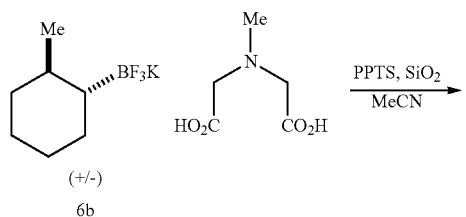

To a 40-mL sealed I-Chem vial under nitrogen was added racemic potassium trans-2-methylcyclohexyltrifluoro borate 6b (1.02 g, 5 mmol), N-methyliminodiacetic acid (MIDA) (2.20 g, 15 mmol), pyridinium p-toluenesulfonate (126 mg, 0.5 mmol) and silica gel (900 mg) followed by acetonitrile (16.7 mL, 0.3 M for the borate). The reaction was sealed and allowed to stir at 80° C. for 12 hours. After cooling down, the mixture was passed through a pad of silica gel before concentration. The light brown solid mixture was then loaded onto a silica gel column and flushed with copious amount of $Et_2O$, the product was then eluted by straight EtOAc. Upon concentration, the product 7b was obtained as a crystalline white solid (1.17 g, 93%).

$^1$H NMR (499 MHz, DMSO) δ 4.17 (d, J=17.0, 1H), 4.10 (d, J=17.0, 1H), 3.98 (d, J=17.0, 1H), 3.93 (d, J=17.0, 1H), 2.89 (s, 3H), 1.66-1.56 (m, 4H), 1.44 (m, 1H) 1.24 (m, 1H), 1.15 (m, 1H), 1.09-0.96 (m, 2H), 0.95 (d, J=6.5, 3H), 0.47 (m, 1H).

$^{13}$C NMR (126 MHz, DMSO) δ 169.2, 168.7, 62.3, 62.0, 45.3, 36.3, 32.2, 26.5, 26.1, 25.3, 22.7.

HRMS (ESI+)

Calculated for $C_{12}H_{21}BNO_4$: 254.1564.

Found: 254.1554.

General Procedure of Hydrolysis of MIDA Boronate

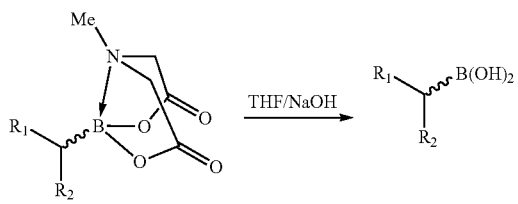

To a stirred solution of MIDA boronate (0.25 mmol) in 2 mL THF under argon was added 2 mL 1 M solution of NaOH. The reaction was allowed to stir at 23° C. for 0.5 h before 4 mL saturated aqueous $NH_4Cl$ was added. Layers were separated and the aqueous layer was extracted with $Et_2O$ three times. The combined ethereal layers were concentrated to near dry (complete dryness might lead to decomposition) and was re-extracted (a small portion of brine could be added if necessary) with $Et_2O$ three times before drying over $Na_2SO_4$ and concentrating to around 200 μL under reduced pressure. The solution was diluted with THF and dried with $Na_2SO_4$ again before concentration to a waxy solid to afford the boronic acid in quantitative yield (0.25 mmol).

b. Synthesis of Enantiomerically-Enriched Boronic Acid (S)-1a

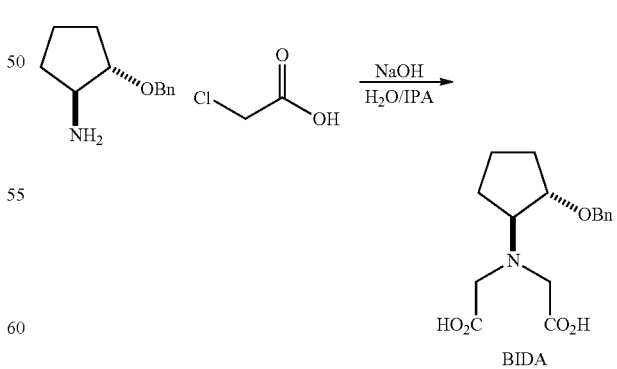

The preparation of benzylcyclopentyl iminodiacetic acid (BIDA) followed the procedure developed previously in our group (Li, J., Burke, M. D. *J. Am. Chem. Soc.*, 2011, 133, 13774).

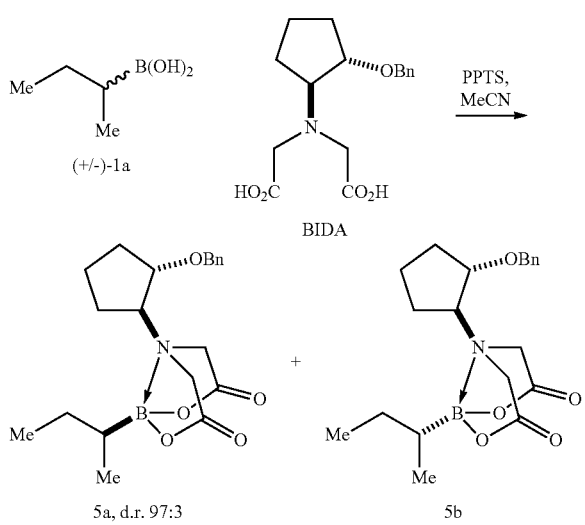

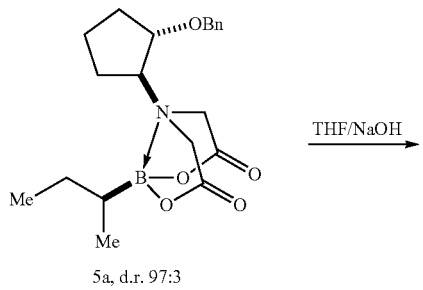

To a 40-mL sealed I-Chem vial under nitrogen was added racemic 2-butyl boronic acid (+/−)-1a (6 mmol), BIDA (4 mmol), pyridinium p-toluenesulfonate (0.4 mmol) followed by acetonitrile (27 mL, 0.15 M for 5). The reaction was allowed to stir at 80° C. for 24 hours. After cooling down, the mixture was passed through a pad of Florisil® before concentration. The light brown solid mixture was then dissolved in $Et_2O$ to make a heterogeneous mixture and filtered; the filtrate was washed with copious amount of $Et_2O$. The white solid was recrystallized with acetone:$Et_2O$ twice to give 5a [463 mg, 97:3 d.r. ($^1H$ NMR) 31%].

TLC: (hexanes:EtOAc=1:1, $KMnO_4$)
Rf=0.41, (S) isomer 5a; Rf=0.16, (R) isomer 5b
$^1H$ NMR (500 MHz, DMSO) δ 8.19 (m, 4H), 8.14 (m, 1H), 5.36 (d, J=11, 1H), 5.30 (d, J=11, 1H), 5.03-4.90 (m, 4H), 4.77 (d, J=17, 1H), 4.35 (q, J=6, 1H), 4.17 (s, 3H), 2.89 (m, 1H), 2.83 (m, 1H), 2.83 (m, 1H), 2.26 (m, 1H), 1.90 (m, 1H), 1.69 (t, J=, 3H), 1.66-1.58 (m, 3H).
$^{13}C$ NMR (125 MHz, DMSO-d6) δ 169.8, 168.3, 137.9, 128.3, 127.8, 127.6, 79.8, 72.1, 70.9, 59.3, 56.4, 39.5, 29.4, 26.2, 24.9, 21.0, 14.2, 12.6.
HRMS (ESI+)
Calculated for $C_{20}H_{29}BNO_5$: 374.2139.
Found: 374.2119.

To a stirred solution of 7 (93 mg, 0.25 mmol) in 2 mL THF under argon was added 2 mL 1 M solution of NaOH. The reaction was allowed to stir at 23° C. for 0.5 h before 4 mL saturated aqueous $NH_4Cl$ was added. Layers were separated and the aqueous layer was extracted with $Et_2O$ three times. The combined ethereal layers were concentrated to near dry (complete dryness might lead to decomposition) and was re-extracted (a small portion of brine could be added if necessary) with $Et_2O$ three times before drying over $Na_2SO_4$ and concentrating to around 200 μL under reduced pressure. The solution was diluted with THF and dried with $Na_2SO_4$ again before concentration to a waxy solid to afford (S)-1a (25 mg, 100%).

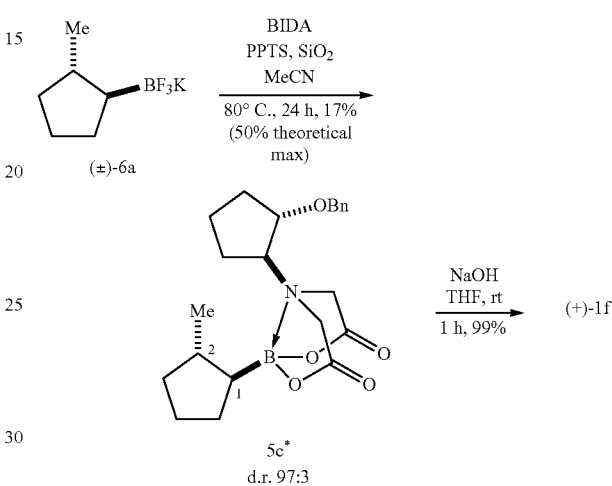

*absolute stereochemistry of 5c at C1 and C2 have not been determined c. General Procedure of Coupling Reactions of Aryl Halides with Alkyl Boronic Acids In the glove box under argon atmosphere, aryl halide (0.10 mmol), boronic acid (0.20 mmol), $Ag_2O$ (70 mg, 0.30 mmol) and $Pd(P(o-tol)_3)_2$ (7.15 mg, 0.010 mmol) were taken up in THF (220 μL) in a 7-mL vial. The reaction was sealed, and stirred at 85° C. for 24 h. The mixture was then passed through a pad of silica gel and flushed with diethyl ether before concentration in vacuo. The desired product was isolated by column chromatography and/or preparative reverse-phase HPLC.

Cross-coupling reactions of aryl halides with alkyl boronic acids

Example 1. (S)-methyl 4-(sec-butyl)benzoate (3a)

Product was isolated as a colorless oil (Br—, 71%; I—, 69%) Enantiomeric ratio (Br—, 85:15, a 88% retention of e.r.; I—, 89:11, a 91% retention of e.r.) was determined by chiral-GC (CP chirasil-DEX CB Column)

$^1$H NMR (500 MHz, Benzene) δ 8.15 (d, J=8.5, 2H), 6.96 (d, J=8.0, 2H), 3.52 (s, 3H), 2.33 (m, 1H), 1.37 (m, 2H), 1.02 (d, J=7.0, 3H), 0.68 (t, J=7.5, 3H).

$^{13}$C NMR (126 MHz, Benzene-d6) δ 166.8, 153.0, 130.2, 127.4, 51.5, 41.9, 31.1, 21.7, 12.3.

HRMS (EI+)

Calculated for $C_{12}H_{16}O_2$: 192.1150.

Found: 192.1141.

The e.r. was determined by chiral-GC using a CP chirasil-DEX CB Column (30 m×320 μm×0.25 μm). Conditions: 75° C., 10 min; 5° C./min to 105° C. and hold, flow rate=1.2255 mL/min, detection wavelength=214 nm. tr(major) 28.5 min, tr(minor) 29.1 min.

Example 2. (S)-2-(sec-butyl)naphthalene (3b)

Product was isolated as a colorless oil (Br—, 84%)

Enantiomeric ratio (Br—, 85:15, a 88% retention of e.r.) was determined by SFC analysis (OD-H Column)

$^1$H NMR (499 MHz, Benzene) δ 7.67 (m, 3H), 7.52 (s, 1H), 7.28 (m, 2H), 7.21 (dd, J=8.0, 1.5, 1H), 2.595 (m, 1H), 1.60 (m, 1H), 1.54 (m, 1H), 1.23 (d, J=7.0, 3H), 0.80 (t, J=7.5, 3H).

$^{13}$C NMR (126 MHz, Benzene) δ 145.1, 134.4, 132.9, 126.1, 126.0, 125.8, 125.4, 42.2, 31.3, 22.1, 12.5.

HRMS (EI+)

Calculated for $C_{14}H_{16}$: 184.1250.

Found: 184.1249.

The e.r. was determined by SFC analysis (OD-H Column) Conditions: 100% $CO_2$, flow rate=2.0 mL/min. detection wavelength=220 nm. tr(major) 9.4 min, tr(minor) 10.3 min.

Example 3. (S)-4-(sec-butyl)-1,1'-biphenyl (3c)

Product was isolated as a colorless oil (Br—, 81%; I—, 83%)

Enantiomeric ratio (Br—, 92:8, a 94% retention of e.r.; I—, 92:8, a 94% retention of e.r.) was determined by SFC analysis (OD-H Column)

$^1$H NMR (500 MHz, Benzene-d6) δ 7.53 (d, J=7.0, 2H), 7.49 (d, J=8.0, 2H), 7.24 (t, J=8.2, 2H), 7.12 (d, J=8.0, 2H), 2.48 (m, 1H), 1.53 (m, 2H), 1.19 (d, J=7.0, 3H), 0.81 (t, J=7.5, 3H).

$^{13}$C NMR (125 MHz, Benzene-d6) δ 146.8, 141.8, 139.4, 129.0, 127.5, 127.4, 127.2, 41.7, 31.5, 22.1, 12.5.

HRMS (EI+)

Calculated for $C_{16}H_{18}$: 210.1409.

Found: 210.1414.

The e.r. was determined by SFC analysis (OD-H Column) Conditions: 100% $CO_2$, flow rate=2.0 mL/min. detection wavelength=220 nm. tr(major) 12.3 min, tr(minor) 15.8 min.

Example 4. (S)-3-(sec-butyl)-1,1'-biphenyl (3d)

Product was isolated as a colorless oil (Br—, 82%)

Enantiomeric ratio (Br—, 93:7, a 96% retention of e.r.) was determined by SFC analysis (OD-H Column)

$^1$H NMR (499 MHz, Benzene) δ 7.54 (m, 2H), 7.43 (t, J=2.0, 1H), 7.38 (m, 1H), 7.24 (t, J=15.5, 3H), 7.06 (m, 1H), 2.50 (m, 1H), 1.55 (m, 1H), 1.49 (m, 1H), 1.19 (d, J=7.0, 3H), 0.80 (t, J=7.5, 3H).

$^{13}$C NMR (126 MHz, Benzene) δ 148.3, 142.2, 141.9, 129.2, 129.0, 127.7, 127.4, 126.5, 126.3, 125.3, 42.2, 31.5, 22.2, 12.5.

HRMS (EI+)

Calculated for $C_{16}H_{18}$: 210.1409.

Found: 210.1410.

The e.r. was determined by SFC analysis (OD-H Column) Conditions: 100% $CO_2$, flow rate=2.0 mL/min. detection wavelength=220 nm. tr(major) 12.3 min, tr(minor) 15.8 min.

Example 5. (S)-1-(sec-butyl)-4-(tert-butyl)benzene (3f)

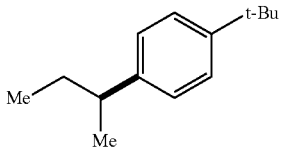

Product was isolated as a colorless oil (Br—, 31%; I—, 61%)

$^1$H NMR (499 MHz, Benzene) δ 7.31 (d, J=8.5, 2H), 7.11 (d, J=8.5, 2H), 2.489 (m, 1H), 2.47 (m, 1H), 1.504 (m, 1H), 1.258 (s, 9H), 1.20 (d, J=7.0, 3H), 0.81 (t, J=7.5, 3H).

$^{13}$C NMR (126 MHz, Benzene) δ 148.6, 144.7, 127.1, 125.5, 41.6, 34.4, 31.6, 31.6, 22.3, 12.5.

HRMS (EI+)
Calculated for $C_{12}H_{22}$: 190.1722.
Found: 190.1727.

Example 6. Methyl 4-cyclopropylbenzoate (3g)

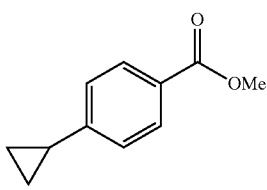

Product was isolated as a colorless oil (Br—, 95%)

$^1$H NMR (499 MHz, Benzene) δ 8.09 (d, J=8.5, 2H), 6.79 (d, J=8.0, 2H), 3.52 (s, 3H), 1.53-1.48 (m, 1H), 0.66-0.63 (m, 2H), 0.47-0.44 (m, 2H).

$^{13}$C NMR (126 MHz, Benzene) δ 166.8, 149.8, 130.1, 125.7, 51.5, 51.5, 15.9, 10.3.

HRMS (EI+)
Calculated for $C_{11}H_{12}O_2$: 176.0837.
Found: 176.0834.

Example 7. Methyl 4-cyclobutylbenzoate (3h)

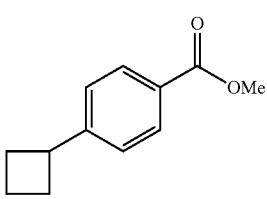

Product was isolated as a colorless oil (Br—, 95%)

$^1$H NMR (500 MHz, Benzene) δ 8.17 (d, J=8.0, 2H), 6.99 (D, J=8.0, 2H), 3.52 (s, 3H), 3.22 (quint, J=9.0, 1H), 2.09-2.02 (m, 2H), 1.94-1.85 (m, 2H), 1.81-1.71 (m, 1H), 1.66-1.58 (m, 1H).

$^{13}$C NMR (126 MHz, Benzene) δ 166.8, 151.5, 130.0, 128.5, 126.6, 51.5, 40.5, 29.7, 18.5.

HRMS (EI+)
Calculated for $C_{12}H_{14}O_2$: 190.0994.
Found: 190.0992.

Example 8. Methyl 4-cyclopentylbenzoate (3i)

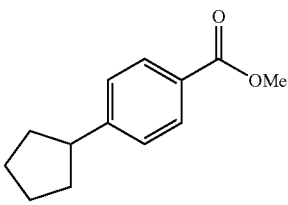

Product was isolated as a colorless oil (Br—, 76%)

$^1$H NMR (499 MHz, Benzene) δ 8.16 (d, J=8.0, 2H), 7.04 (d, J=8.5, 2H), 3.53 (s, 3H), 2.73-2.65 (m, 1H), 1.84-1.77 (m, 2H), 1.63-1.55 (m, 2H), 1.50-1.41 (m, 2H), 1.40-1.32 (m, 2H).

$^{13}$C NMR (126 MHz, Benzene) δ 166.8, 152.0, 130.1, 127.5, 51.5, 51.5, 46.2, 34.7, 25.8.

HRMS (EI+)
Calculated for $C_{13}H_{16}O_2$: 204.1150.
Found: 204.1147.

Example 9. Methyl 4-cyclohexylbenzoate (3j)

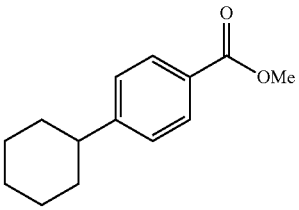

Product was isolated as a colorless oil (Br—, 69%)

$^1$H NMR (499 MHz, Benzene) δ 8.17 (d, J=8.5, 2H), 7.01 (d, J=8.5, 2H), 3.53 (s, 3H), 2.27 (m, 1H), 1.66 (m, 4H), 1.63-1.59 (m, 1H), 1.24-1.17 (m, 5H).

$^{13}$C NMR (126 MHz, Benzene) δ 166.8, 153.3, 130.2, 127.2, 51.5, 44.8, 34.3, 27.0, 26.3.

HRMS (EI+)
Calculated for $C_{14}H_{18}O_2$: 218.1307.
Found: 204.1309.

Example 10. Methyl 4-((1S,2S)-2-methylcyclopentyl)benzoate ((±)-3k)

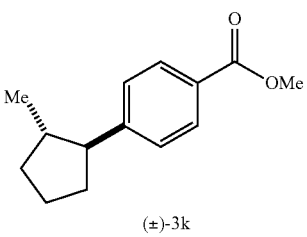

¹H NMR (500 MHz, Benzene) δ 8.17 (d, J=8.5, 2H), 7.02 (d, J=8.5, 2H), 3.53 (s, 3H), 2.20-2.14 (m, 1H), 1.90-1.77 (m, 2H), 1.73-1.64 (m, 1H), 1.61-1.48 (m, 3H), 1.17-1.09 (m, 1H), 0.82 (d, J=6.5, 3H).

¹³C NMR (126 MHz, Benzene) δ 166.8, 151.0, 130.2, 54.7, 51.5, 43.3, 35.4, 35.0, 24.1, 18.5.

HRMS (EI+)

Calculated for $C_{14}H_{18}O_2$: 218.1307.

Found: 218.1306.

Example 11. 4-((1S,2S)-2-methylcyclopentyl)-1,1'-biphenyl ((±)-3l)

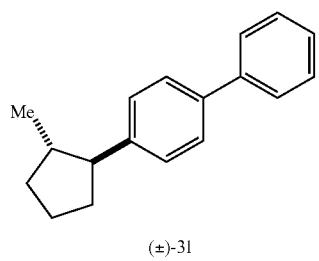

(±)-3l

¹H NMR (500 MHz, Benzene) δ 7.55 (m, 2H), 7.51 (m, 2H), 7.24 (m, 2H), 2.34-2.28 (m, 1H), 2.05-1.99 (m, 1H), 1.92-1.80 (m, 2H), 1.73-1.59 (m, 3H), 1.25-1.19 (m, 1H), 0.94 (d, J=6.0, 3H).

¹³C NMR (126 MHz, Benzene) δ 144.6, 141.8, 139.5, 129.1, 127.6, 127.4, 127.3, 54.6, 43.3, 35.7, 35.0, 24.2, 18.7.

HRMS (EI+)

Calculated for $C_{18}H_{20}$: 236.1565.

Found: 236.1565.

Example 12. Methyl 4-((1S,2S)-2-methylcyclohexyl)benzoate ((±)-3m)

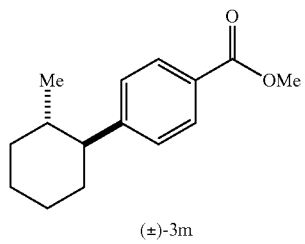

(±)-3m

Product was isolated as a colorless oil (Br—, 65%)

¹H NMR (500 MHz, Benzene) δ 8.16 (d, J=8.5, 2H), 6.97 (d, J=8.5, 2H), 3.53 (s, 3H), 1.88 (td, J=11.0, 3.0, 1H), 1.68-1.61 (m, 4H), 1.38-1.30 (m, 1H), 1.28-1.12 (m, 3H), 0.97-0.88 (m, 1H), 0.61 (d, J=6.5, 3H).

¹³C NMR (126 MHz, Benzene) δ 166.8, 152.3, 130.2, 128.8, 128.1, 52.7, 51.4, 37.6, 35.9, 35.5, 27.1, 26.9, 20.9.

HRMS (EI+)

Calculated for $C_{15}H_{20}O_2$: 232.1463.

Found: 232.1466.

Example 13. 4-((1S,2S)-2-methylcyclohexyl)-1,1'-biphenyl ((±)-3n)

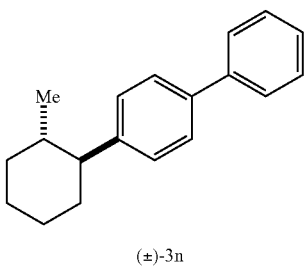

(±)-3n

Product was isolated as a colorless oil (I—, 62%)

¹H NMR (499 MHz, Benzene) δ 7.55 (m, 1H), 7.53 (m, 1H), 7.51 (d, J=8.5, 2H), 7.24 (m, 2H), 7.13 (m, 3H), 2.01 (td, J=11.0, 3.5, 1H), 1.83 (m, 1H), 1.76-1.69 (m, 3H), 1.54-1.45 (m, 1H), 1.44-1.22 (m, 3H), 1.06-0.97 (m, 1H), 0.76 (d, J=6.5, 3H).

¹³C NMR (126 MHz, Benzene) δ 146.2, 141.8, 139.4, 129.0, 127.5, 127.4, 127.2, 52.5, 38.0, 36.1, 36.0, 27.3, 27.1, 21.1.

HRMS (EI+)

Calculated for $C_{19}H_{22}$: 250.1721.

Found: 250.1724.

Example 14

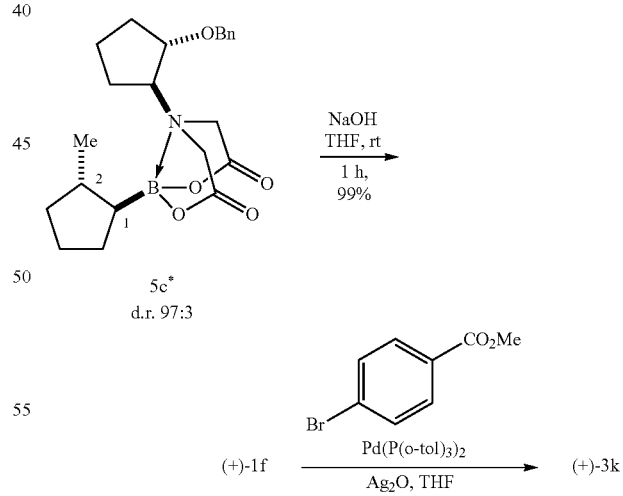

*absolute stereochemistry of 5c at C1 and C2 have not been determined

Product (+)-3k was isolated as a colorless oil (54%).

Enantiomeric ratio (Br—, 97:3, a 99% retention of e.r.) was determined by chiral-GC (CP chirasil-DEX CB Column)

The e.r. was determined by chiral-GC using a CP chirasil-DEX CB Column (30 m × 320 μm×0.25 μm).

Conditions: 75° C., 10 min; 1° C./min to 120° C. and hold, flow rate=1.2255 mL/min, detection wavelength=214 nm. tr(major) 70.2 min, tr(minor) 73.3 min.

The optical rotation of (+)-1f was determined to be $[\alpha]^{23}{}_D$+14.4 (THF, e.e. =94% based on 5b). The optical rotation of (+)-3k was determined to be $[\alpha]^{23}{}_D$+46.0 (benzene, e.e. =94% based on chiral-GC).

d. Determination of the Absolute Stereochemistry of 3a and 3b

The absolute stereochemistry of compounds 3a-3c was determined by comparison of the optical rotation to the literature value. All products correspond to net retention in the cross-coupling reaction.

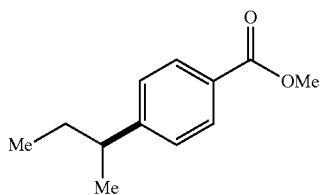

3a (S)-3a, $[\alpha]^{23}{}_D$ + 21.0
(EtOH, e.e. = 78% based on chiral GC)
lit: (R)-3a, $[\alpha]^{25}{}_D$ - 19.02
(EtOH, e.e. = 65%)
(Menicagli R., Piccolo,
O. J. Org. Chem., 1980, 45, 2581)

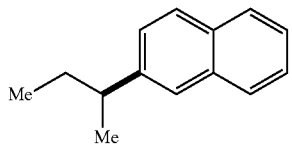

3b (S)-3b, $[\alpha]^{23}{}_D$ + 24.5
(benzene, e.e. = 70% based on SFC)
lit: (R)-3b, $[\alpha]^{23}{}_D$ + 33.3
(neat, e.e. = 94%)
((a) Piccolo, O. et al. *Tetrahedron*
1979, 35, 1751;
(b) Taylor, B. L. et al *J. Am.*
*Chem. Soc.* 2011, 133, 389)

III. Determination of Benchtop Stability of Boronic Acids and MIDA Boronates

The stability of 2-butyl boronic acid and 2-butyl BIDA boronates to storage as solids under air at 23° C. was quantified using the following general procedure: Two 7-mL vials were charged with 10 mg of freshly prepared boronic acid or BIDA boronate at 23° C. under ambient atmosphere. The vials containing these solid samples were then sealed with PTFE-lined screwcaps under ambient atmosphere and placed on the bench top at 23° C. The solid sample present in one of the vials was then immediately analyzed by $^1$H-NMR to verify the purity and quantity of boronic acid present at time zero (the NMR assay is described below). After 1 day (boronic acid) or 60 days (BIDA boronates), the solid sample in the second vial was analyzed by $^1$H-NMR, again by the method described below, to determine the quantity of boronic acid remaining at the indicated time.

NMR assay: An NMR stock solution was prepared as follows: To a 25 mL volumetric flask was added bromoacetophenone (0.336 g, 1.69 mmol, internal standard for quantification of the boronic acid), tetramethylsilane (1 mL, internal standard for the NMR shifts), and DMSO-d6:D$_2$O 95:5 to a final solution volume of 25.0 mL. To a vial containing solid boronic acid or solid BIDA boronate (see above) was added 1.00 mL of this NMR stock solution, and the resulting solution was analyzed by $^1$H-NMR. The mmol of boronic acid or MIDA boronate present in the sample was determined by comparing the ratio of the integrated 4-bromoacetophenone aryl C—H doublets (7.90 ppm relative to TMS) to that of the boronic acid or MIDA boronate C—H signals.

IV. Direct Conversion to Trihydroxyboronate Salt

In another embodiment, racemic secondary alkylboronic acids such as 1a undergo complexation with the chiral derivative of iminodiacetic acid, 8. The resulting diastereomers are resolved by recrystallization. Chiral boronate 5a is then converted to the sodium trihydroxyborate salt 12. Salt 12 was found to be stable to isolation and storage at room temperature, unlike the unstable boronic acid 1a. By treating 12 with BF$_3$OEt$_2$, 1a is obtained as a dioxane solution a form that is competent for cross-coupling. This procedure was found to be highly reproducible, giving nonracemic 1a in a pure form that is competent for cross-coupling, containing no oligomerized boroxine or other impurities resulting from degradation of 1a. We then demonstrate stereoretentive Suzuki cross-coupling of 1a to obtain representative chiral aromatic compounds 3a and 3c in enantioenriched form.

Example 15. Step 1

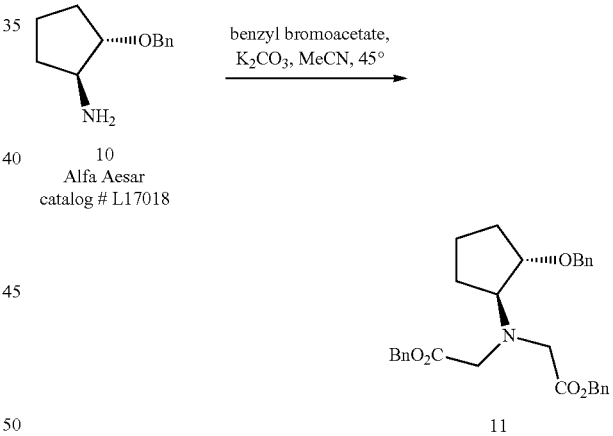

(1S,2S)-(+)-2-Benzyloxycyclopentylamine, 99% ee: 957 mg (5 mmol), benzyl bromoacetate, 96%: 2.74 g (11.5 mmol), K$_2$CO$_3$: 3.36 g (24.3 mmol), MeCN: 17 mL To a 3-neck flask containing K$_2$CO$_3$ and a stir bar, and fitted with a reflux condensor, added MeCN, then substrate 10, then benzyl bromoacetate. The mixture was stirred at 45° C. under nitrogen. After 16 hours, full conversion seen by TLC using 100% EtOAc and KMnO$_4$ stain. The mixture was filtered through Celite with EtOAc washings and concentrated by rotary evaporation. The resulting yellow oil was purified by silica gel chromatography using a gradient of 10% to 30% EtOAc in hexanes. 11 was collected and concentrated under vacuum for 16 hours to 2.23 g viscous oil, 91%.

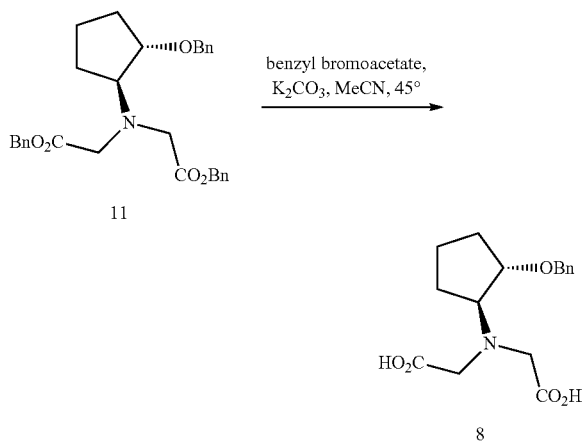

substrate 11: 2.44 g (5 mmol), 10% Pd on carbon: 1.2 g, 1,4-cyclohexadiene: 4.9 mL (50 mmol), absolute EtOH: 50 mL To a 3-neck flask containing palladium on carbon and a stir bar under nitrogen, added 40 mL EtOH, then 11. The substrate was transferred with an additional 10 mL of EtOH. Added cyclohexadiene by syringe. Stirred at room temperature. The reaction exothermed to 30° C. The reaction was complete at 2 hours as seen by TLC using 1:4 H₂O:acetone and cerium ammonium molybdate stain. 100 mL of MeOH was added to dissolve the white precipitate. The catalyst was filtered off by passing the mixture through Celite while keeping under N₂ and washing through with EtOH. The flow-through was concentrated by rotary evaporation to 1.4 g of 8 as a white solid, 91%. No purification was necessary.

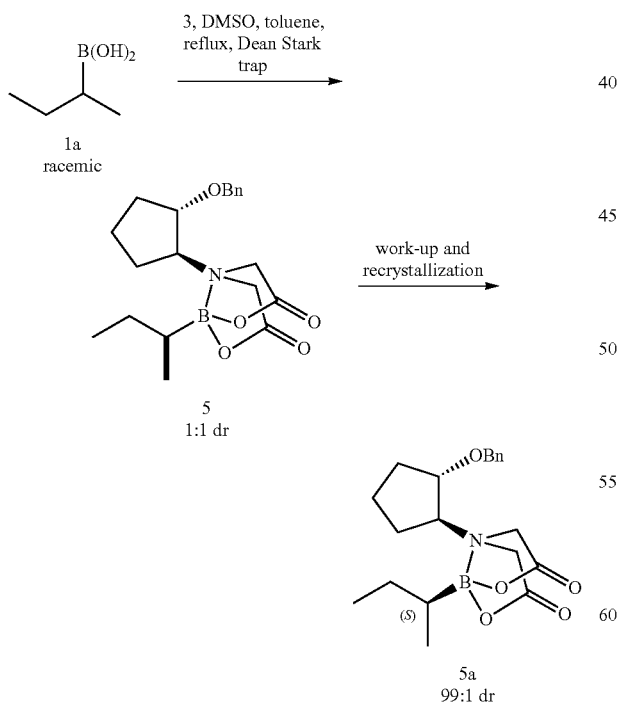

2-butylboronic acid: 2.80 g (27.5 mmol), 3: 7.04 g (22.9 mmol), DMSO: 23 mL, toluene: 207 mL Racemic 1a, obtained from Sigma Aldrich, was combined with DMSO, toluene, and 8 in a round-bottom flask with a stir bar. The flask was fitted with a Dean-Stark trap and reflux condensor. The mixture was stirred at reflux in an oil bath at 170° C. under air with continuous removal of water. After 3 hours, conversion was complete by TLC using 1:1 EtOAc:hexanes and KMnO₄ stain. The toluene was removed by rotary evaporation. 200 mL of DCM and 200 mL were added to the resulting DMSO suspension. In a separatory funnel, the aqueous layer was extracted four times with DCM. The combined DCM phase was washed with water five times, then once with brine. It was then dried with sodium sulfate and concentrated by rotary evaporation. The resulting solid was dissolved in acetone and passed through silica in a glass frit. The flow-through was again concentrated under vacuum. The crude 5, 1:1 dr, was dissolved in 40 mL of dry acetone with heating. 80 mL of Et₂O was slowly added to this stirred solution, causing a white precipitate. This was stirred 10 hours and the solids were filtered. This white solid, 2.55 g, was dissolved in 17 mL acetone. 34 mL Et₂O was slowly added, causing precipitation. The suspension was stirred 5 hours, then the solids were collected by filtration. 1.79 g of 5a was obtained as a white solid. 21% yield. ¹H-NMR in CDCl₃ showed a diastereomeric ratio of 99:1. The absolute stereochemistry of the 2-butyl stereocenter was determined by x-ray crystallography.

Compound 8 was recovered from the combined concentrated flow-through from the above procedure. The combined solid, 6.64 g, was combined with 12 mL of 3 M NaOH and 12 mL THF and stirred at room temperature until complete hydrolysis was seen by TLC. The THF was removed under rotary evaporation. 8.5 mL of saturated NH₄Cl was added. In a separatory funnel, this solution was washed three times with 15 mL of Et₂O. The Et₂O residue was removed under an air stream, then the solution was acidified to pH 3 with 6 M HCl, causing precipitation to form. The suspension was stirred in an ice bath for 1 hour, then the solids were collected by filtration and dried under vacuum to give 4.04 g of recovered 8

Step 2

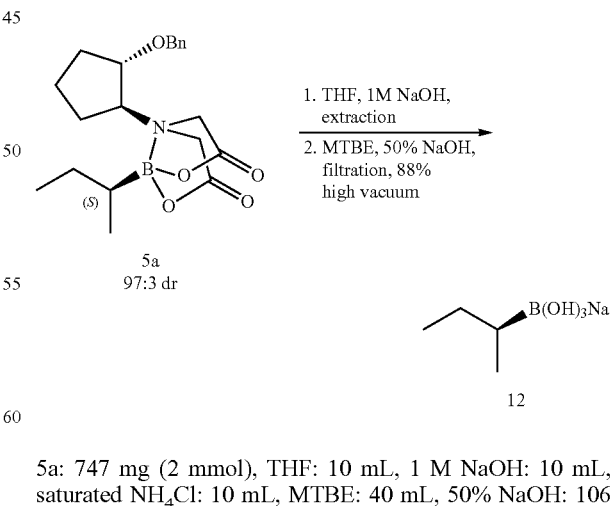

5a: 747 mg (2 mmol), THF: 10 mL, 1 M NaOH: 10 mL, saturated NH₄Cl: 10 mL, MTBE: 40 mL, 50% NaOH: 106 μL (2 mmol)

5a was stirred in a round-bottom flask with 10 mL THF and 10 mL NaOH until complete conversion as seen by TLC using 1:1 EtOAc:Hexanes and KMnO₄ stain. THF was thoroughly removed under rotary evaporation with 40° C. bath. 10 mL of saturated NH₄Cl was added and the solution was extracted four times with 10 mL of MTBE in a reparatory funnel. The combined MTBE phase was dried over Na₂SO₄ and concentrated by rotary evaporation to a volume of 10 mL. To this solution was added 106 µL of 50% NaOH over 1 minute with rapid stirring. The suspension was stirred 20 minutes at room temperature, then the solids were collected by filtration through a medium glass frit. The solids were washed with 2 mL of MTBE and dried under vacuum at 1 torr for 12 hours to give 12 in 88% yield as a white solid.

12 was analyzed by NMR by the following procedure. 14.2 mg (0.1 mmol) of 12 was added to an NMR tube with 500 µL of CD₃OD containing 0.1 M 1,4-dimethoxybenzene as an internal standard. ¹H-NMR was taken with the d1 parameter set to 10 seconds. The hydroxyl peak appears at 4.95 ppm. The signals of the standard were integrated to 4H and 6H. A second spectrum of 500 µL of CD₃OD was taken and the signals of the standard were integrated to 4H and 6H. The integration of the hydroxyl peak and 4.95 ppm was subtracted from the corresponding peak in the spectrum of 12. The value obtained was 2.7H, indicating no excess water or sodium hydroxide present in the sample of 12.

Step 3

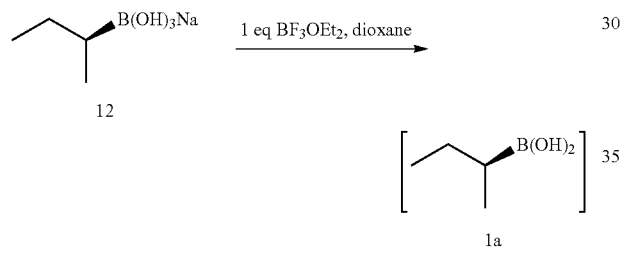

12: 114 mg (0.8 mmol), BF₃OEt₂: 99 µL (1.4 mmol), 1,4-dioxane: 0.6 mL 12 was added to a 2 mL vial with 400 µL dioxane and a stir bar. In the hood, the vial was opened to the air and BF₃OEt₂ was added over 1 minute with 1300 rpm stirring. The vial was capped and stirred 30 minutes at room temperature. The slurry was filtered through 40 mg of Celite over a cotton plug in a 5 inch Pasteur pipette. The vial was washed with 200 µL dioxane and passed through the Celite with an air hose, giving 440 µL of solution. 50 µL of the homogeneous dioxane solution was withdrawn and added to 500 µL of DMSO-d₆ containing 0.1 M 1,4-dimethoxybenzene standard. ¹H-NMR with d1 set to 10 seconds showed the concentration of the boronic acid 1a to be 1.32 M. Yield was calculated to be 72%.

Step 4

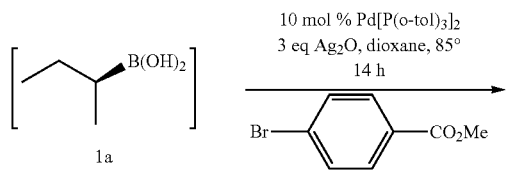

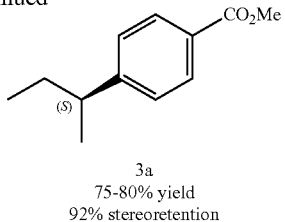

3a
75-80% yield
92% stereoretention

1a: 0.2 mmol, aryl bromide: 21.5 mg (0.1 mmol), catalyst: 7.2 mg (0.01 mmol), Ag₂O: 70 mg (0.3 mmol), dioxane: 0.22 mL In a glovebox, the catalyst, aryl bromide and Ag₂O were added to a 7 mL vial with a stir bar. 151 µL (0.2 mmol) of a 1.32 M solution of 1a in dioxane was added by mechanical pipette. 69 µL of additional dioxane was added and the vial was tightly capped and stirred at 85° C. for 14 hours. The reaction was opened and filtered through a silica plug in a Pasteur pipette with three washings of 1 mL of Et₂O. The flow-through was concentrated under vacuum and 500 µL of benzene-d₆ containing 0.1 M 1,4-dimethoxybenzene was added. The solution was analyzed by ¹H-NMR to determine yield. Percent stereoretention was calculated by subtracting the percent of the major enantiomer of 3a from the percent of the major enantiomer of 1a. Then that quantity was subtracted from 100 to give percent stereoretention. The stereoretention was found to be 92%. Yield was 75%. The e.r. was determined by chiral-GC using a CP chirasil-DEX CB Column (30 m x 320 µm x 0.25 µm). Conditions: 75° C., 10 min; 5° C./min to 105° C. and hold. Enantiomers of 3a eluted at 32.9 minutes and 34.0 minutes.

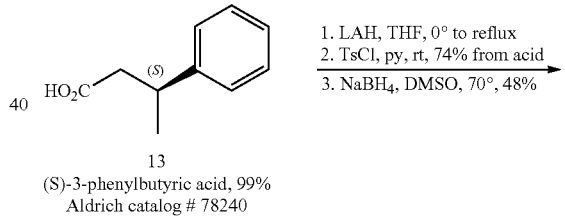

13
(S)-3-phenylbutyric acid, 99%
Aldrich catalog # 78240

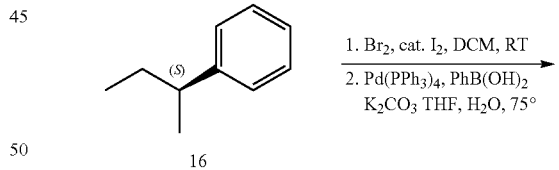

16

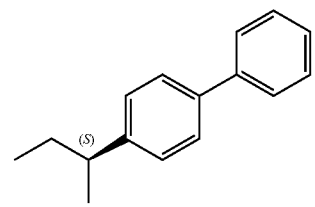

>99:1 er
3c (S)-3-phenylbutyric acid: 331 mg (2 mmol), LAH, 95%: 88 mg (2.2 mmol), THF: 13.5 mL The substrate was added to a round-bottom flask under N₂ with a reflux condenser containing LAH and THF. The mixture was stirred at reflux for 15 hours. Aqueous Rochelle salt and water were added to quench the reaction. The reaction was extracted three times with DCM. The combined organic phase was dried with Na$_2$SO$_4$ and concentrated under vacuum. The residue was filtered through a silica plug with EtOAc and concentrated again to 311 mg oil. This alcohol (S)-3-phenylbutan-1-ol (14) was used directly in the next step.

14: 310 mg (2.0 mmol), pyridine: 1 mL, toluenesulfonyl chloride: 419 mg (2.2 mmol)

14 was combined with pyridine and TsCl in a 40 mL capped vial and stirred at room temperature for 5 hours until complete conversion was seen by TLC. 1 M HCl was added and the reaction was extracted three times with Et$_2$O. The combined organic phase was washed with 1 M HCl, H$_2$O, saturated NaHCO$_3$, and dried with Na$_2$SO$_4$ and concentrated under vacuum. The crude was purified by silica column using 5% to 15% EtOAc in hexanes. 460 mg of tosylate 15 ((S)-3-phenylbutyl 4-methylbenzenesulfonate) was obtained as a colorless oil, 74% yield from 9.

15: 450 mg (1.45 mmol), NaBH$_4$: 281 mg (7.25 mmol), DMSO: 8 mL 15 was combined with DMSO and NaBH$_4$ in a 20 mL vial and stirred under N$_2$ at 70° C. for 14 hours. After complete consumption of 15, the reaction was quenched with H$_2$O and extracted four times with n-pentane. The pentane phase was washed with water three times and dried with Na$_2$SO$_4$. This was concentrated under light vacuum to give 16 as a colorless oil. 128 mg, 48%. $[\alpha]^{20}_D$=+27.4° (c=1.0, CHCl$_3$)

16: 27 mg (0.2 mmol), I$_2$: 2.5 mg (0.01 mmol), Br$_2$: 12.4 µL (0.24 mmol), DCM: 0.5 mL 16 was combined with iodine and DCM in a 7 mL vial. Neat bromine was added dropwise in an ice bath with stirring. The reaction was stirred at room temperature open to the air for 2 hours, then quenched with 0.5 M KOH. The reaction was extracted three times with DCM, then dried with Na$_2$SO$_4$ and concentrated under vacuum. NMR showed a 1:1 ratio of 16 to 4-bromo-[1-(2-butyl)]benzene. This mixture was used directly in the next step.

Crude mixture: 23 mg, Pd(PPh$_3$)$_4$: 1.7 mg (0.0015 mmol), phenylboronic acid: 24 mg (0.2 mmol), K$_2$CO$_3$: 236 mg (1.7 mmol), THF: 0.8 mL, H$_2$O: 0.57 mL All reagents except water were combined in a 20 mL vial in a glovebox. In the hood, water was added and the headspace was purged with N$_2$ before capping and stirring at room temperature for 10 hours at 75° C. TLC in 100% pentane shows desired product. The THF was removed under vacuum and the aqueous phase was extracted with pentane three times. The pentane extracts were dried with Na$_2$SO$_4$ and concentrated under vacuum. Product was purified by silica column using 100% pentane. 12.3 mg colorless oil obtained. $^1$H-NMR showed this to be 3c with minor impurities.

Example 16

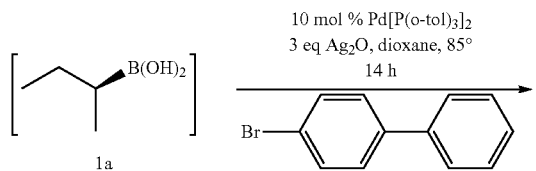

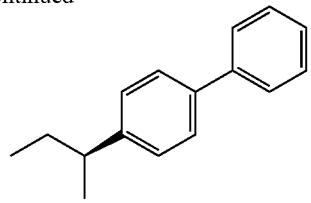

3c
68% yield
94% stereoretention

Compound 3c was synthesized by the same cross-coupling procedure as described above in Example 15 for the synthesis of 3a. The sample of 1a was made from resolved 5 of 97:3 dr. The absolute stereochemistry of 3c was determined by chiral HPLC comparison to 3c and racemic 3c. NMR spectrum was identical to that of 3c. Racemic 3c was prepared by cross-coupling of racemic 1a by the same procedure as described for the synthesis of 3a. A Chiralcel OD-H column was used, eluting with 100% n-heptane at 1.2 mL/minute and detection at 220 nm and 254 nm. (S) retention time: 9.5 min. (R) retention time: 14.6 min.

EQUIVALENTS

One of ordinary skill in the art will appreciate that starting materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

Although the present disclosure has been described with reference to certain embodiments thereof, other embodiments are possible without departing from the present disclosure. The spirit and scope of the appended claims should not be limited, therefore, to the description of the preferred embodiments contained herein. All embodiments that come within the meaning of the claims, either literally or by equivalence, are intended to be embraced therein. Furthermore, the advantages described above are not necessarily the only advantages of the disclosure, and it is not necessarily expected that all of the described advantages will be achieved with every embodiment of the disclosure.

INCORPORATION BY REFERENCE

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

We claim:

1. A method of forming a chiral non-racemic secondary boronic acid, comprising:
combining a chiral compound of formula (I)

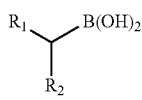

wherein, independently for each occurrence, $R^1$ and $R^2$ are selected from the group consisting of substituted $C_1$-$C_6$ alkyl and unsubstituted $C_1$-$C_6$ alkyl; a chiral iminodiacetic acid, wherein the chiral iminodiacetic acid is not a racemic mixture; pyridinium p-toluenesulfonate (PPTS); and a polar aprotic solvent, thereby forming a mixture of chiral boronates;
resolving the mixture of chiral boronates into individual diastereomers; and
hydrolyzing an individual diastereomer,
thereby forming the chiral non-racemic secondary boronic acid.

2. The method of claim 1, wherein the hydrolyzing is with aqueous hydroxide.

3. The method of claim 1, wherein the chiral iminodiacetic acid has an enantiomeric excess of at least 80 percent.

4. The method of claim 1, wherein the chiral iminodiacetic acid is benzylcyclopentyl iminodiacetic acid (BIDA).

5. The method of claim 1, wherein the chiral non-racemic secondary boronic acid has an enantiomeric excess of at least 80 percent.

6. The method of claim 1, wherein the resolving is by crystallization.

7. The method of claim 1, wherein the resolving is by chromatography.

8. The method of claim 1, wherein the hydrolyzing is with aqueous NaOH.

9. The method of claim 1, wherein the chiral iminodiacetic acid has an enantiomeric excess of at least 90 percent.

10. The method of claim 1, wherein the chiral iminodiacetic acid has an enantiomeric excess of at least 95 percent.

11. The method of claim 1, wherein the polar aprotic solvent is $CH_3CN$.

12. The method of claim 1, wherein the compound of formula (I) is a racemic mixture.

13. The method of claim 1, wherein the compound of formula (I) is not a racemic mixture.

14. The method of claim 1, wherein the chiral non-racemic secondary boronic acid has an enantiomeric excess of at least 90 percent.

15. The method of claim 1, wherein the chiral non-racemic secondary boronic acid has an enantiomeric excess of at least 95 percent.

16. The method of claim 1, wherein the chiral non-racemic secondary boronic acid has an enantiomeric excess of at least 80 percent; and the chiral iminodiacetic acid has an enantiomeric excess of at least 80 percent.

17. The method of claim 1, wherein the chiral non-racemic secondary boronic acid has an enantiomeric excess of at least 90 percent; and the chiral iminodiacetic acid has an enantiomeric excess of at least 90 percent.

18. The method of claim 1, wherein the chiral non-racemic secondary boronic acid has an enantiomeric excess of at least 95 percent; and the chiral iminodiacetic acid has an enantiomeric excess of at least 95 percent.

19. The method of claim 1, wherein the chiral non-racemic secondary boronic acid has an enantiomeric excess of at least 80 percent; the chiral iminodiacetic acid has an enantiomeric excess of at least 80 percent; and the compound of formula (I) is a racemic mixture.

20. The method of claim 1, wherein the chiral non-racemic secondary boronic acid has an enantiomeric excess of at least 90 percent; the chiral iminodiacetic acid has an enantiomeric excess of at least 90 percent; and the compound of formula (I) is a racemic mixture.

21. The method of claim 1, wherein the chiral non-racemic secondary boronic acid has an enantiomeric excess of at least 95 percent; the chiral iminodiacetic acid has an enantiomeric excess of at least 95 percent; and the compound of formula (I) is a racemic mixture.

22. The method of claim 1, wherein the chiral non-racemic secondary boronic acid has an enantiomeric excess of at least 95 percent; the chiral iminodiacetic acid has an enantiomeric excess of at least 95 percent; and the chiral iminodiacetic acid is benzylcyclopentyl iminodiacetic acid (BIDA).

23. The method of claim 1, wherein the chiral non-racemic secondary boronic acid has an enantiomeric excess of at least 95 percent; the chiral iminodiacetic acid has an enantiomeric excess of at least 95 percent; the chiral iminodiacetic acid is benzylcyclopentyl iminodiacetic acid (BIDA); and the compound of formula (I) is a racemic mixture.

24. The method of claim 1, wherein the chiral non-racemic secondary boronic acid has an enantiomeric excess of at least 95 percent; the chiral iminodiacetic acid has an enantiomeric excess of at least 95 percent; the chiral iminodiacetic acid is benzylcyclopentyl iminodiacetic acid (BIDA); the compound of formula (I) is a racemic mixture; and the hydrolyzing is with aqueous hydroxide.

25. The method of claim 1, wherein the chiral non-racemic secondary boronic acid has an enantiomeric excess of at least 95 percent; the chiral iminodiacetic acid has an enantiomeric excess of at least 95 percent; the chiral iminodiacetic acid is benzylcyclopentyl iminodiacetic acid (BIDA); the compound of formula (I) is a racemic mixture; and the hydrolyzing is with aqueous NaOH.

26. The method of claim 1, wherein the chiral non-racemic secondary boronic acid has an enantiomeric excess of at least 95 percent; the chiral iminodiacetic acid has an enantiomeric excess of at least 95 percent; the chiral iminodiacetic acid is benzylcyclopentyl iminodiacetic acid (BIDA); the compound of formula (I) is a racemic mixture; the hydrolyzing is with aqueous NaOH; and the polar aprotic solvent is $CH_3CN$.

* * * * *